United States Patent
Dale et al.

(10) Patent No.: US 9,498,228 B2
(45) Date of Patent: Nov. 22, 2016

(54) APPARATUS AND METHOD FOR HEART VALVE REPAIR

(71) Applicant: St. Jude Medical, Cardiology Division, Inc., St. Paul, MN (US)

(72) Inventors: Theodore Paul Dale, Corcoran, MN (US); Richard J. Olson, Blaine, MN (US); Benjamin E. Morris, Jeffersonville, IN (US); John Miser, Crestwood, KY (US)

(73) Assignee: St. Jude Medical, Inc., St. Paul, MN (US)

( * ) Notice: Subject to any disclaimer, the term of this patent is extended or adjusted under 35 U.S.C. 154(b) by 260 days.

(21) Appl. No.: 14/271,974

(22) Filed: May 7, 2014

(65) Prior Publication Data

US 2014/0243856 A1    Aug. 28, 2014

Related U.S. Application Data

(62) Division of application No. 13/363,778, filed on Feb. 1, 2012, now Pat. No. 8,777,966.

(60) Provisional application No. 61/438,446, filed on Feb. 1, 2011.

(51) Int. Cl.
*A61B 17/10* (2006.01)
*A61B 17/128* (2006.01)
(Continued)

(52) U.S. Cl.
CPC ..... *A61B 17/1285* (2013.01); *A61B 17/00234* (2013.01); *A61B 17/0218* (2013.01);
(Continued)

(58) Field of Classification Search
CPC .......... A61B 17/12013; A61B 17/128; A61B 17/1285; A61B 2017/00243; A61B 2017/00349; A61B 2017/00353; A61B 2017/00358; A61B 2017/00367; A61B 2017/00371; A61B 2017/00783; A61B 2017/2933
See application file for complete search history.

(56) References Cited

U.S. PATENT DOCUMENTS 5,156,608 A   10/1992   Troidl et al.
5,499,991 A   3/1996    Garman et al.
(Continued)

FOREIGN PATENT DOCUMENTS

AU   2002300522 B2   1/2007
WO   9620749 A1      7/1996
(Continued)

OTHER PUBLICATIONS

International Search Report and Written Opinion for Application No. PCT/US2013/065360 dated Apr. 23, 2014.
(Continued)

*Primary Examiner* — Robert Lynch
(74) *Attorney, Agent, or Firm* — Lerner, David, Littenberg, Krumholz & Mentlik, LLP

(57) ABSTRACT

A transcatheter method of gathering tissue of a heart valve leaflet may include inserting an elongated catheter assembly to a position adjacent the heart valve leaflet, the catheter assembly including a capture tool moveable between a retracted position and an extended position, a tissue support, and a clamping member moveable between an open position and a closed position. The capture tool may be partially retracted to gather tissue of the heart valve leaflet between the tissue support and the clamping member. The clamping member may then be moved from the open position toward the closed position so as to clamp a substantial portion of the gathered tissue of the heart valve leaflet between the tissue support and the clamping member. Subsequently, a clip may be applied from the catheter assembly to the clamped tissue so as to hold the clamped tissue substantially in a gathered configuration.

19 Claims, 17 Drawing Sheets

(51) Int. Cl.
    *A61B 17/122*  (2006.01)
    *A61B 17/02*   (2006.01)
    *A61B 17/064*  (2006.01)
    *A61B 17/12*   (2006.01)
    *A61B 17/00*   (2006.01)
    *A61B 17/29*   (2006.01)

(52) U.S. Cl.
    CPC ......... *A61B17/0644* (2013.01); *A61B 17/122* (2013.01); *A61B 17/12013* (2013.01); *A61B 17/128* (2013.01); *A61B 2017/00243* (2013.01); *A61B 2017/00349* (2013.01); *A61B 2017/00353* (2013.01); *A61B 2017/00783* (2013.01); *A61B 2017/00867* (2013.01); *A61B 2017/0645* (2013.01); *A61B 2017/0649* (2013.01); *A61B 2017/2933* (2013.01)

(56) References Cited

U.S. PATENT DOCUMENTS

| | | |
|---|---|---|
| 5,601,573 A | 2/1997 | Fogelberg et al. |
| 5,741,278 A | 4/1998 | Stevens |
| 5,749,879 A | 5/1998 | Middleman et al. |
| 5,921,993 A | 7/1999 | Yoon |
| 6,440,152 B1 | 8/2002 | Gainor et al. |
| 6,569,182 B1 | 5/2003 | Balceta et al. |
| 6,626,930 B1 | 9/2003 | Allen et al. |
| 6,752,813 B2 | 6/2004 | Goldfarb et al. |
| 6,945,978 B1 | 9/2005 | Hyde |
| 7,011,669 B2 | 3/2006 | Kimblad |
| 7,464,712 B2 | 12/2008 | Oz et al. |
| 7,569,062 B1 | 8/2009 | Kuehn et al. |
| 7,758,595 B2 | 7/2010 | Allen et al. |
| 8,777,966 B2 | 7/2014 | Dale et al. |
| 8,951,285 B2 | 2/2015 | Sugimoto et al. |
| 2001/0016750 A1 | 8/2001 | Malecki et al. |
| 2002/0010388 A1 | 1/2002 | Taylor et al. |
| 2002/0013571 A1 | 1/2002 | Goldfarb et al. |
| 2002/0035390 A1 | 3/2002 | Schaldach et al. |
| 2002/0049457 A1 | 4/2002 | Kaplan et al. |
| 2002/0107531 A1 | 8/2002 | Schreck et al. |
| 2002/0183768 A1 | 12/2002 | Deem et al. |
| 2003/0093071 A1 | 5/2003 | Hauck et al. |
| 2004/0030335 A1 | 2/2004 | Zenati et al. |
| 2004/0039442 A1 | 2/2004 | St. Goar et al. |
| 2004/0087985 A1 | 5/2004 | Loshakove et al. |
| 2004/0176784 A1 | 9/2004 | Okada |
| 2004/0181238 A1 | 9/2004 | Zarbatany et al. |
| 2004/0193185 A1 | 9/2004 | McBrayer |
| 2005/0004583 A1* | 1/2005 | Oz ............... A61B 17/064 606/142 |
| 2005/0090837 A1 | 4/2005 | Sixto et al. |
| 2005/0096671 A1 | 5/2005 | Wellman et al. |
| 2005/0107871 A1 | 5/2005 | Realyvasquez et al. |
| 2005/0125011 A1 | 6/2005 | Spence et al. |
| 2005/0143763 A1 | 6/2005 | Ortiz et al. |
| 2005/0149072 A1 | 7/2005 | DeVries et al. |
| 2005/0177176 A1 | 8/2005 | Gerbi et al. |
| 2005/0251161 A1 | 11/2005 | Saadat et al. |
| 2006/0089671 A1 | 4/2006 | Goldfarb et al. |
| 2006/0122633 A1 | 6/2006 | To et al. |
| 2006/0173422 A1 | 8/2006 | Reydel et al. |
| 2006/0173473 A1 | 8/2006 | Bob |
| 2007/0049952 A1 | 3/2007 | Weiss |
| 2007/0093857 A1 | 4/2007 | Rogers et al. |
| 2007/0102474 A1 | 5/2007 | Shelton et al. |
| 2007/0102475 A1 | 5/2007 | Ortiz et al. |
| 2007/0142846 A1 | 6/2007 | Catanese et al. |
| 2007/0162056 A1 | 7/2007 | Gerbi et al. |
| 2007/0197858 A1 | 8/2007 | Goldfarb et al. |
| 2007/0198032 A1* | 8/2007 | Ortiz ............... A61B 17/076 606/138 |
| 2007/0225734 A1 | 9/2007 | Bell et al. |
| 2008/0125796 A1 | 5/2008 | Graham |
| 2008/0255427 A1 | 10/2008 | Satake et al. |
| 2008/0294175 A1 | 11/2008 | Bardsley et al. |
| 2008/0300624 A1 | 12/2008 | Schwemberger et al. |
| 2008/0319455 A1 | 12/2008 | Harris et al. |
| 2009/0062852 A1 | 3/2009 | Marino |
| 2009/0118744 A1 | 5/2009 | Wells et al. |
| 2009/0125038 A1 | 5/2009 | Ewers et al. |
| 2009/0149870 A1 | 6/2009 | Jugenheimer et al. |
| 2011/0054521 A1 | 3/2011 | Ventura et al. |
| 2011/0077668 A1 | 3/2011 | Gordon et al. |
| 2011/0087242 A1 | 4/2011 | Pribanic et al. |
| 2011/0114700 A1 | 5/2011 | Baxter, III et al. |
| 2011/0230897 A1 | 9/2011 | Palermo et al. |
| 2011/0313432 A1 | 12/2011 | Miles et al. |
| 2012/0109159 A1 | 5/2012 | Jordan et al. |
| 2012/0226291 A1 | 9/2012 | Malizia et al. |
| 2013/0046332 A1 | 2/2013 | Jones et al. |
| 2014/0039607 A1 | 2/2014 | Kovach |

FOREIGN PATENT DOCUMENTS

| | | |
|---|---|---|
| WO | 9900059 A1 | 1/1999 |
| WO | 0128432 A1 | 4/2001 |
| WO | 0139672 A2 | 6/2001 |
| WO | 0182847 A2 | 11/2001 |
| WO | 0200121 A1 | 1/2002 |
| WO | 03049619 A2 | 6/2003 |
| WO | 2006039199 A2 | 4/2006 |
| WO | 2007027451 A2 | 3/2007 |
| WO | 2008068756 A2 | 6/2008 |
| WO | 2008121738 A2 | 10/2008 |
| WO | 2009087592 A2 | 7/2009 |
| WO | 2010094896 A1 | 8/2010 |
| WO | 2011053673 A1 | 5/2011 |
| WO | 2012087724 A1 | 6/2012 |
| WO | 2012106398 A1 | 8/2012 |
| WO | 2013019415 A1 | 2/2013 |
| WO | 2013116617 A1 | 8/2013 |
| WO | 2014022464 A1 | 2/2014 |

OTHER PUBLICATIONS

International Search Report for Application No. PCT/US2013/052832 dated Jan. 15, 2014.
Merriam-Webster definition of "fabric" as accessed on Dec. 17, 2014; http://www.merriam-webster.com/dictionary/fabric.
International Preliminary Report on Patentability for Application No. PCT/US2012/023437 dated Aug. 6, 2013.
International Search Report and Written Opinion for Application No. PCT/US2013/023082 dated Oct. 1, 2013.
International Search Report and Written Opinion for Application No. PCT/US2013/024304 dated Jul. 5, 2013.
International Search Report and Written Opinion for Application No. PCT/US2013/052822 dated Jan. 21, 2014.
International Search Report and Written Opinion for Application No. PCT/US2013/052838 dated Oct. 11, 2013.
International Search Report and Written Opinion for Application No. PCT/US2013/052843 dated Oct. 11, 2013.
International Search Report for Application No. PCT/US2012/023437 dated Apr. 24, 2012.
International Search Report for Application No. PCT/US2013/023077 dated May 14, 2013.

* cited by examiner

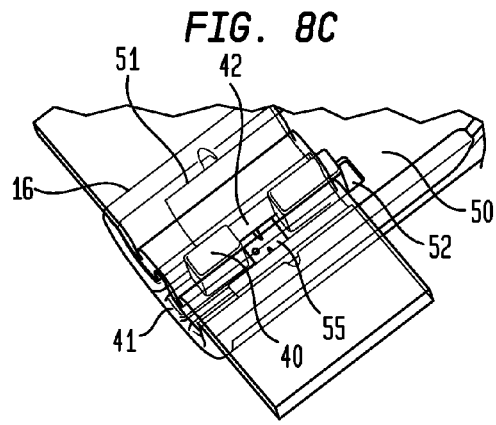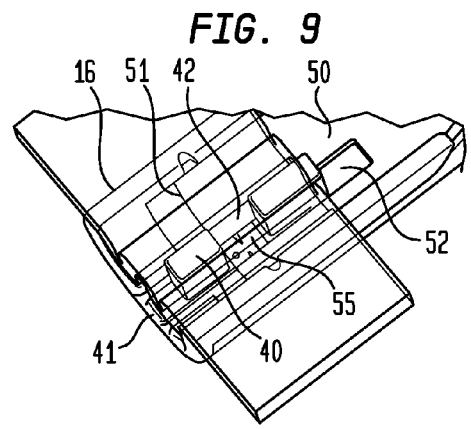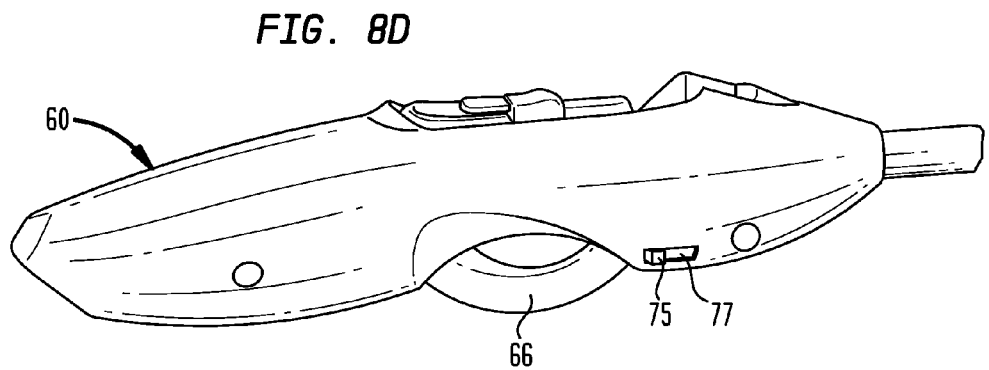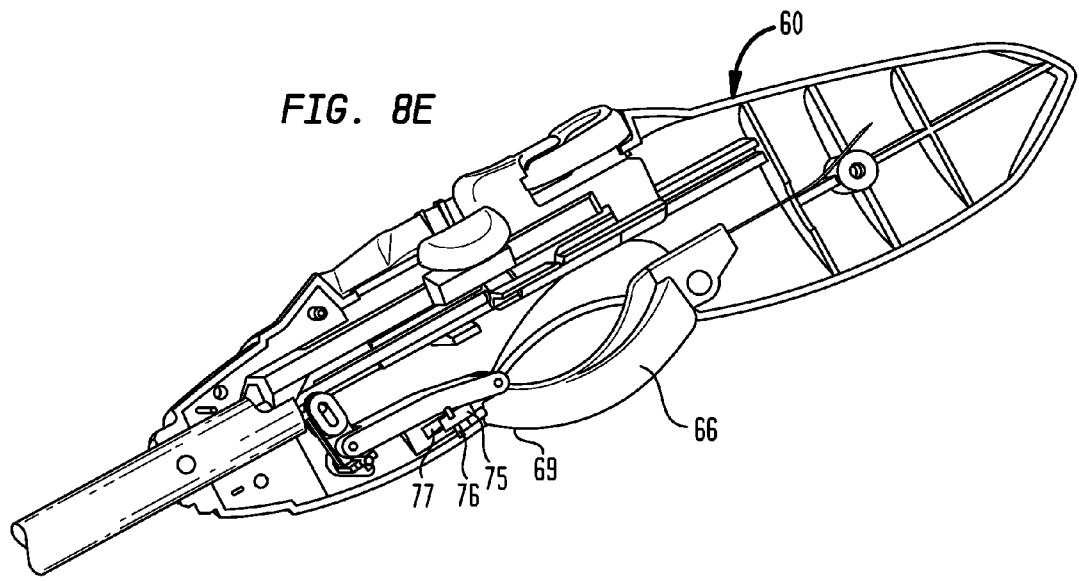

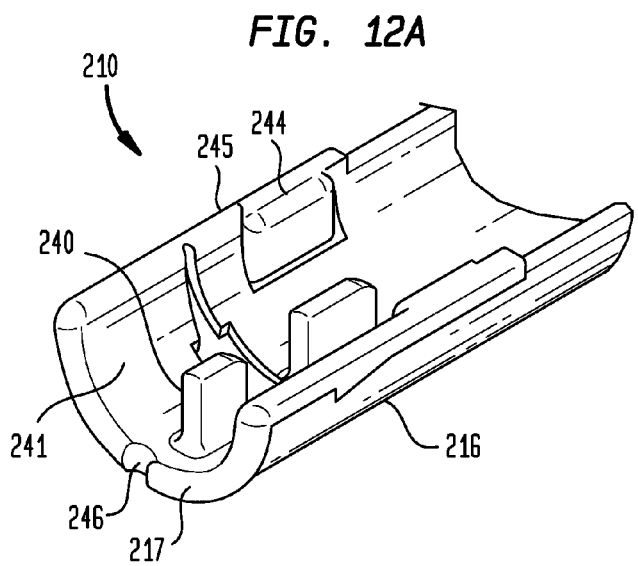
FIG. 12A
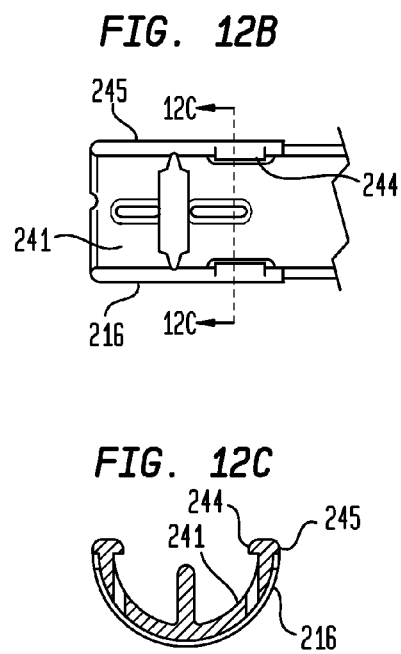
FIG. 12B
FIG. 12C
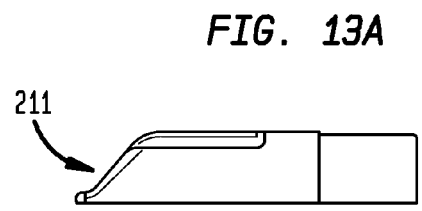
FIG. 13A
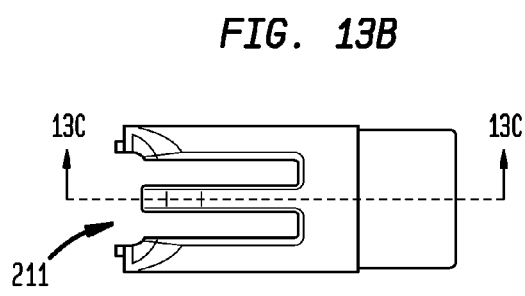
FIG. 13B
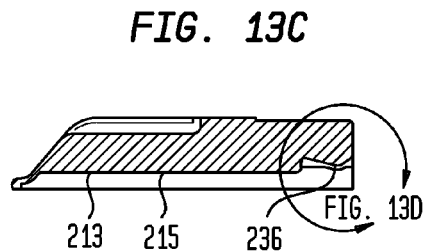
FIG. 13C
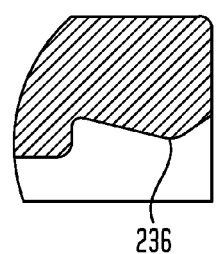
FIG. 13D

APPARATUS AND METHOD FOR HEART VALVE REPAIR

CROSS-REFERENCE TO RELATED APPLICATION

The present application is a divisional of U.S. patent application Ser. No. 13/363,778, filed Feb. 1, 2012, which claims the benefit of U.S. Provisional Patent Application Ser. No. 61/438,446, filed Feb. 1, 2011, entitled "Apparatus and Method for Heart Valve Repair," the disclosures of which are hereby incorporated herein by reference.

BACKGROUND OF THE INVENTION

The present invention is related to heart valve repair, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendinae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendinae may stretch and thus become too long, or the chordae tendinae may be broken. As a result, the valve does not close normally. As a result of being stretched, the unsupported valve leaflet bulges back, or "prolapses," into the left atrium like a parachute. Thus, as the ventricle contracts, the abnormal leaflet may be propelled backwards, beyond its normal closure line into the left atrium, thereby allowing blood to return back into the left atrium and the lungs.

Mitral valve prolapse causes mitral regurgitation. Isolated posterior leaflet prolapse of the human heart mitral valve, i.e. prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

Patents relevant to devices, systems, and methods for transcatheter repair of heart valve leaflets include U.S. Pat. Nos. 6,752,813, 7,464,712, and 7,758,595.

BRIEF SUMMARY OF THE INVENTION

Methods and devices for transcatheter gathering of heart valve leaflet tissue are disclosed.

A transcatheter method of gathering tissue of a heart valve leaflet may include inserting an elongated catheter assembly to a position adjacent the heart valve leaflet, the catheter assembly including a capture tool moveable between a retracted position and an extended position, a tissue support, and a clamping member moveable between an open position spaced from the tissue support and a closed position adjacent the tissue support. The capture tool may be moved from the retracted position to the extended position. The clamping member may then be moved from an initial position to the open position adjacent the heart valve leaflet. The catheter assembly may be manipulated so that tissue of the heart valve leaflet is positioned between the tissue support and the clamping member. The capture tool may then be partially retracted from the extended position toward the retracted position to gather an additional amount of tissue of the heart valve leaflet between the tissue support and the clamping member. The clamping member may then be moved from the open position toward the closed position so as to clamp a substantial portion of the gathered tissue of the heart valve leaflet between the tissue support and the clamping member, the clamped tissue having a gathered configuration. Subsequently, a clip may be applied from the catheter assembly to the clamped tissue so as to hold the clamped tissue substantially in the gathered configuration.

A distal end of the capture tool may have a hook shape. The capture tool may extend in a longitudinal direction, and a distal end of the capture tool may include an arm extending in a direction transverse to the longitudinal direction, the arm having a serrated edge. The capture tool may include a grasping wire slidably disposed in a containment tube. The method may further include sliding a distal portion of the grasping wire out from the containment tube so that the distal portion of the grasping wire changes from a linear shape to a hook shape. The grasping wire may be made from a memory metal material.

A distal portion of the clamping member may have a fork shape. The catheter assembly may extend in a longitudinal direction. The step of moving the clamping member from the initial position to the open position may include moving a distal portion of the clamping member distally in the longitudinal direction and laterally away from the tissue support in a direction transverse to the longitudinal direction. The step of moving the clamping member from the open position toward the closed position may include moving the distal portion of the clamping member further distally in the longitudinal direction and laterally toward the tissue support in a direction transverse to the longitudinal direction. The step of moving the clamping member from the initial position to the open position may include sliding a first cam surface of the clamping member against a guide surface fixed relative to the catheter assembly to cause the distal portion of the clamping member to move laterally away from the tissue support. The step of moving the clamping member from the open position toward the closed position may include sliding a second cam surface of the clamping member against the guide surface to cause the distal portion of the clamping member to move laterally toward the tissue support.

The catheter assembly may extend in a longitudinal direction. The tissue support may include first and second bodies spaced apart in the longitudinal direction. The gathered configuration may be in the shape of a W. The catheter assembly may further include a retaining arm moveable between a distal position for retaining the clip and a proximal position for releasing the clip. The step of applying the clip may include moving the retaining arm from the distal position to the proximal position, whereby the clip may be released for application to the clamped tissue. The clip may be biased from an open condition to a clamping condition. The retaining arm may hold the clip in the open condition. The step of moving the retaining arm from the distal position to the proximal position may release the clip for movement to the clamping condition.

The catheter assembly may further include an operating handle having a first actuating member moveable in opposite longitudinal directions. The step of moving the capture tool from the retracted position to the extended position may include moving the first actuating member in a first one of the longitudinal directions. The capture tool may include a grasping wire slidably disposed in a containment tube. The first actuating member may have first and second portions that are moveable relative to one another in the longitudinal directions. The step of moving the capture tool from the retracted position to the extended position may further include moving the second portion relative to the first portion to slide a distal portion of the grasping wire out from the containment tube so that the distal portion of the grasping wire changes from a linear shape to a hook shape.

The step of partially retracting the capture tool may include moving the first actuating member in a second one of the longitudinal directions opposite the first longitudinal direction. The operating handle may include a second actuating member moveable in the opposite longitudinal directions. The step of moving the clamping member from the initial position to the open position may include moving the second actuating member in the first longitudinal direction. The step of moving the clamping member from the open position toward the closed position may include moving the second actuating member further in the first longitudinal direction. The operating handle may include a third actuating member moveable in a direction transverse to the longitudinal directions. The step of applying the clip may include moving the third actuating member in the direction transverse to the longitudinal directions.

A device for transcatheter gathering of tissue of a heart valve leaflet may include an elongated tube, a capture tool moveable in the tube between a retracted position and an extended position, a tissue support located within a distal portion of the tube, and a clamping member moveable in the tube between an open position spaced from the tissue support and a closed position adjacent the tissue support. The capture tool and the clamping member may be operable to gather and clamp tissue of the heart valve leaflet between the tissue support and the clamping member, such that the clamped tissue has a gathered configuration.

A distal end of the capture tool may have a hook shape. The capture tool may extend in a longitudinal direction. A distal end of the capture tool may include an arm extending in a direction transverse to the longitudinal direction, the arm having a serrated edge. The capture tool may include a grasping wire slidably disposed in a containment tube. A distal portion of the grasping wire may be adapted to change from a linear shape to a hook shape when the distal portion of the grasping wire is extended out from the containment tube. The elongated tube may include a support element having a contact surface facing a contact surface of the tissue support. The support element and the tissue support may be adapted to cooperate to prevent movement of the containment tube in a direction perpendicular to a longitudinal axis of the elongated tube. The grasping wire may be made from a memory metal material. The device may include an operating handle having an actuating member adapted to control movement of the capture tool between the retracted and extended positions. The actuating member may have first and second portions that are moveable relative to one another. The first portion may be adapted to control movement of the grasping wire. The second portion may be adapted to control movement of the containment tube.

A distal portion of the clamping member may have a fork shape. The distal portion of the clamping member may have two tines having respective ends that are spaced apart from one another by an internal gap. The clamping member may include first and second cam surfaces. The tube may include a guide surface fixed relative to the tube. The first cam surface may be adapted to slide against the guide surface to pivot a distal portion of the clamping member away from the tissue support when the clamping member moves in a first direction from an initial position to the open position. The second cam surface may be adapted to slide against the guide surface to pivot the distal portion of the clamping member toward the tissue support when the clamping member moves further in the first direction from the open position to the closed position. The device may include an operating handle having an actuating member adapted to control movement of the clamping member between the open and closed positions.

The tube may extend in a longitudinal direction. The tissue support may include first and second bodies spaced apart in the longitudinal direction. The gathered configuration may be in the shape of a W. The device may include a releasable clip adapted to be applied to the clamped tissue for holding the clamped tissue in the gathered configuration. The device may include a retaining arm moveable between a distal position for retaining the clip and a proximal position for releasing the clip for application to the clamped tissue. The clip may be biased from an open condition to a clamping condition. The retaining arm in the distal position may hold the clip in the open configuration. The retaining arm in the proximal position may release the clip for application to the clamped tissue. The outer tube may include tabs that are adapted to prevent movement of the retaining arm in a direction perpendicular to a longitudinal axis of the elongated tube. The device may include an operating handle having an actuating member adapted to control movement of the retaining arm between the distal position and the proximal position.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

FIG. 8C is a view similar to FIG. 8A, but with portions removed to illustrate the interior of the distal portion;

FIGS. 8D and 8E are a perspective view and a longitudinal cross-sectional view of the handle of FIG. 2B, shown with the buttons positioned to correspond to the positions of the components of the device shown in FIG. 8A;

FIG. 9 is a view similar to FIG. 8C, but shown with the retaining arm in a partially-retracted position;

FIG. 12A is a perspective view of a variant of the distal portion of the outer tube of FIG. 4A;

FIG. 12B is a top view of the outer tube of FIG. 12A;

FIG. 12C is a cross-sectional view taken along line B-B of FIG. 12B;

FIG. 13A is a side view of a component that provides an alternative embodiment of the pin of FIG. 4B;

FIG. 13B is a top view of the component of FIG. 13A;

FIG. 13C is a cross-sectional view taken along line A-A of FIG. 13B;

FIG. 13D is an enlarged view of the contact surface of FIG. 13C;

DETAILED DESCRIPTION

As used herein, the terms "proximal" and "distal" are to be taken as relative to a user (e.g., a surgeon or an interventional cardiologist) using the disclosed transcatheter devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1:
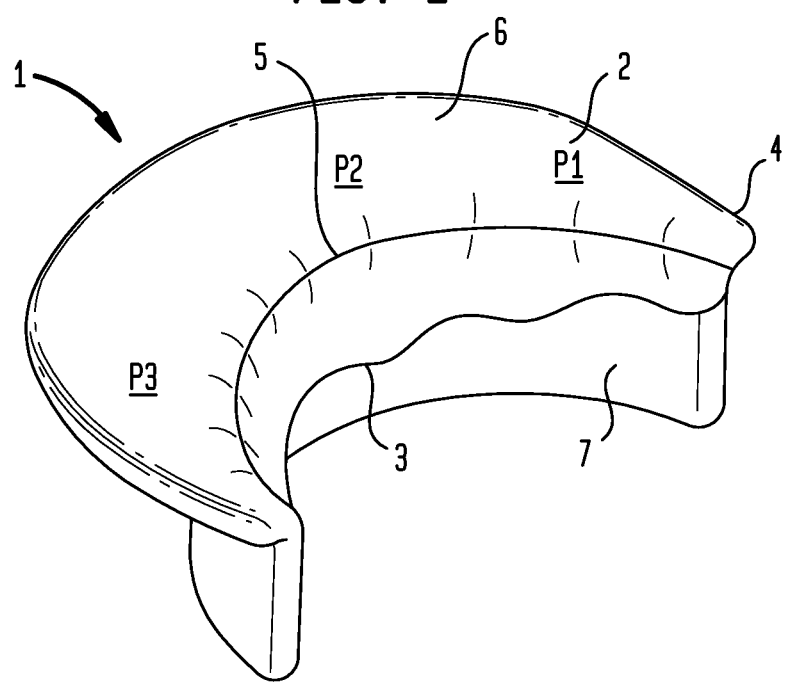
FIG. 1 is a diagrammatic perspective view of the posterior leaflet of a mitral valve.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus 4 and the coaption line 5. Additionally, the posterior leaflet 2 has a lower portion 7 that is generally parallel to the direction of blood flow through the valve 1 and extends below the coaption line 5. The posterior leaflet 2 has three scalloped portions P1, P2, and P3, any of which may include a portion that is billowed, loose, or floppy, and therefore be the cause of a prolapse condition of the valve. The inventive devices, systems, and methods described herein may be adapted to repair such a billowed, loose, or floppy portion of the posterior leaflet 2 or the anterior leaflet 3.

Figure 2A:
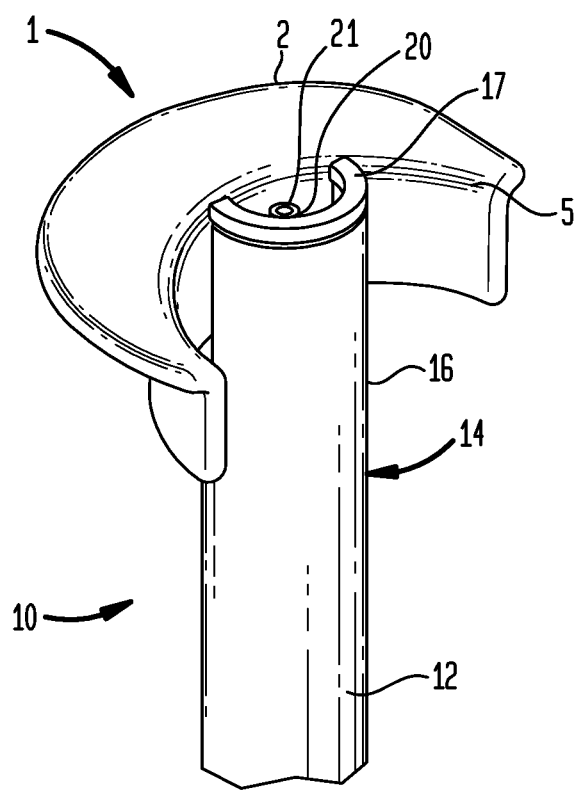
FIG. 2A is a perspective view of the distal portion of one embodiment of a device for transcatheter gathering of heart valve leaflet tissue, engaged with the posterior leaflet of the mitral valve of FIG. 1.

Referring to FIG. 2A, an exemplary device 10 for transcatheter gathering of heart valve leaflet tissue includes an elongated catheter assembly 12 adapted to be inserted through the apex of a human heart so that a distal portion 14 of the catheter assembly may reach the patient's mitral valve 1 for repair thereof.

Figure 3:
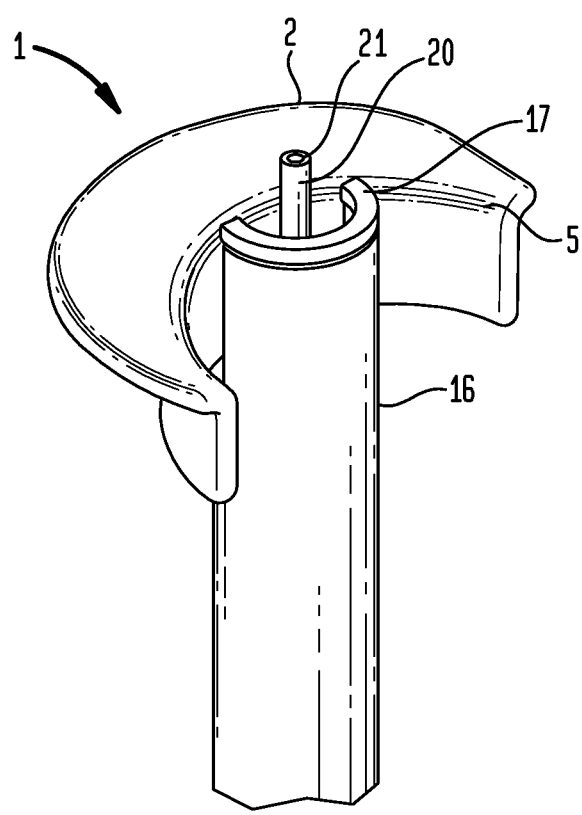
FIG. 3 is a perspective view of the distal portion of the device of FIG. 2A, shown with the containment tube deployed.

The catheter assembly 12 includes a containment tube 20 disposed within an outer tube 16 and longitudinally slidable therein between a retracted position within the outer tube and a deployed position in which a distal tip 21 of the containment tube protrudes distally beyond the distal edge 17 of the outer tube (FIG. 3). In a particular embodiment, the outer tube 16 may be made of one or more echogenic materials, so that the outer tube may be more easily visualized inside a patient using three-dimensional echocardiography.

Figure 4A:
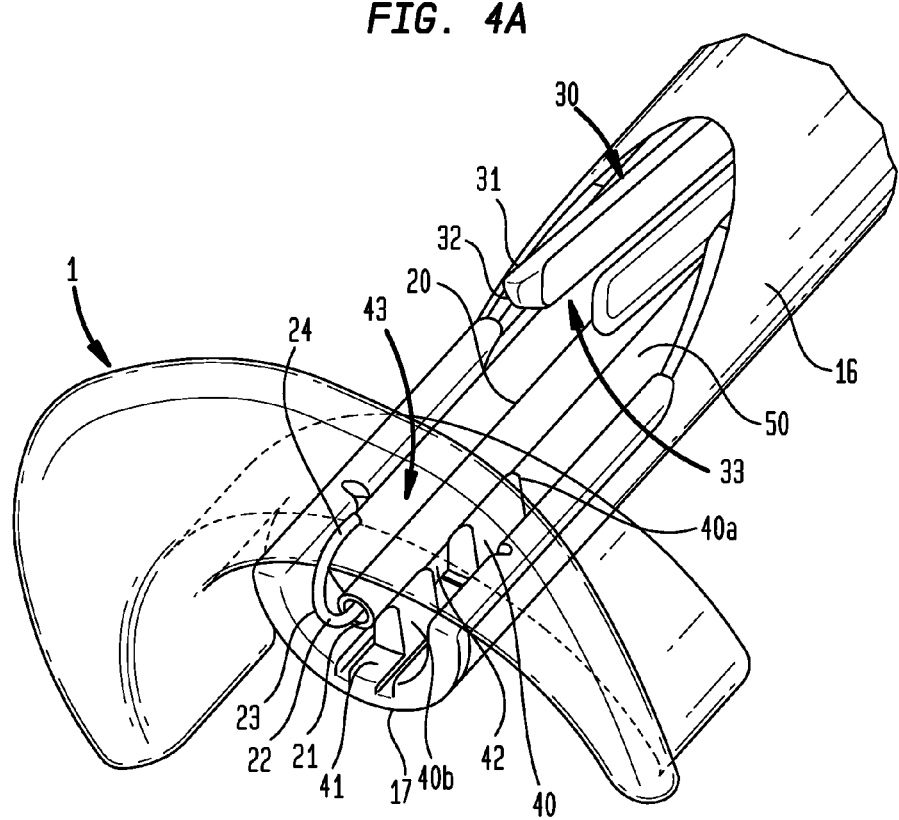
FIGS. 4A and 4B are a perspective view and a longitudinal cross-sectional view of the distal portion of the device of FIG. 2A, shown with the hook deployed.
Figure 4B:
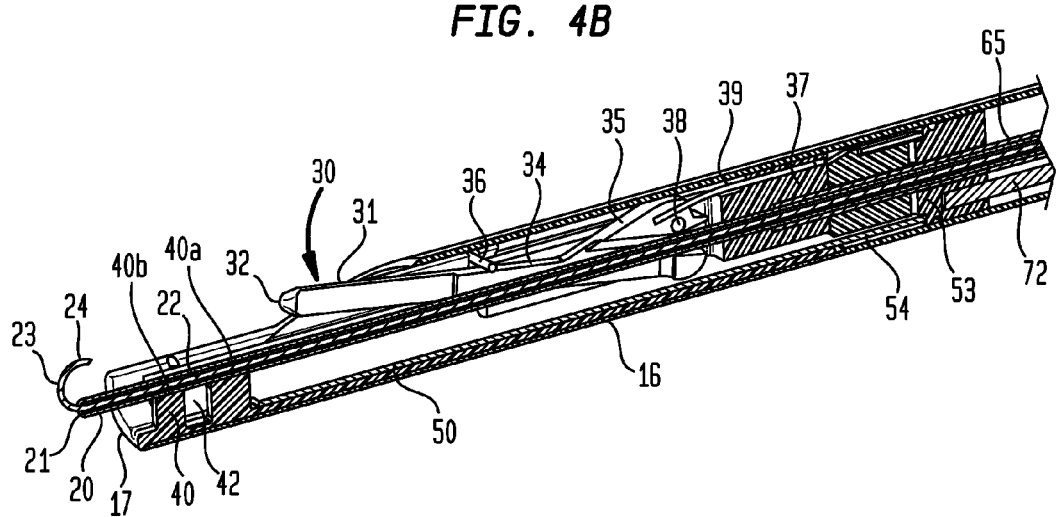

The catheter assembly 12 further includes a capture tool in the form of a grasping wire 22 (FIGS. 4A and 4B) that is longitudinally slidable within the containment tube 20 between a retracted position substantially entirely within the lumen of the containment tube (FIGS. 2 and 3), and a deployed position in which a distal portion 23 of the grasping wire protrudes from the distal tip of the containment tube (FIGS. 4A and 4B). The grasping wire 22 may have a linear configuration when fully retracted within the containment tube 20 and the distal portion 23 thereof may assume the shape of a hook 24 when deployed from the containment tube. In that regard, the grasping wire 22 may be formed from a memory metal or a strong, resilient metal or polymer that will cause the hook 24 to form automatically when deployed.

Figure 8A:
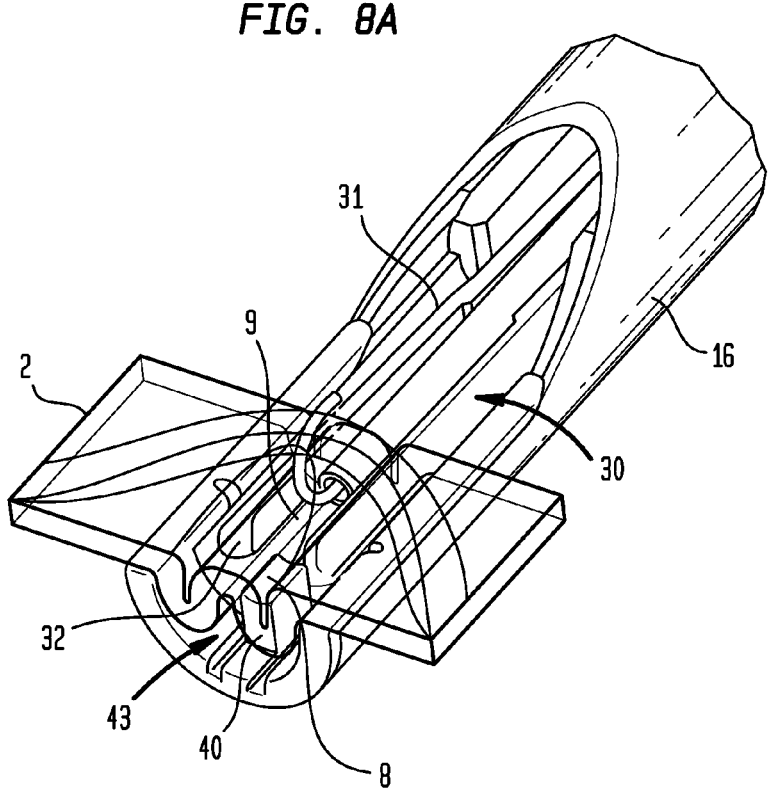
FIGS. 8A and 8B are a perspective view and a longitudinal cross-sectional view of the distal portion of the device of FIG. 2A, shown with the hook in the partially-retracted position and the fork in the tissue-capturing position.

The catheter assembly 12 further includes a clamping member in the form of a fork 30 (FIGS. 4A and 4B) that is longitudinally slidable within the outer tube 16 between an initial or retracted position (FIG. 4A) and a tissue-capturing position (FIG. 8A). The fork 30 includes two tines 31 having respective ends 32, the tines being spaced apart from one another by an internal gap 33. The fork 30 further includes first cam surfaces 34 that are the top surfaces of the tines 31 and a second cam surface 35 located proximally of the tines. The cam surfaces 34 and 35 are adapted to cooperate with a pin 36 attached to the outer tube 16 and orientated substantially orthogonal to the longitudinal direction of travel of the fork 30 to control transverse movement of the fork relative to the outer tube 16, as will be explained below.

At its distal end 17, the outer tube 16 has an open side that provides clearance for the fork 30 to move away from the closed side 41 of the outer tube. A tissue support in the form of an anvil 40 (FIGS. 4A and 4B) is mounted on the closed side 41 of the outer tube 16 so as to lie between the closed side 41 and the containment tube 20 when the containment tube is in the deployed position. The anvil 40 has a proximal portion 40a and a distal portion 40b, with a gap 42 defined therebetween. The widths of the portions 40a and 40b are such that the anvil 40 may be received between the tines 31 of the fork 30 during the use of the device 10 to repair the valve leaflet.

Figure 10A:
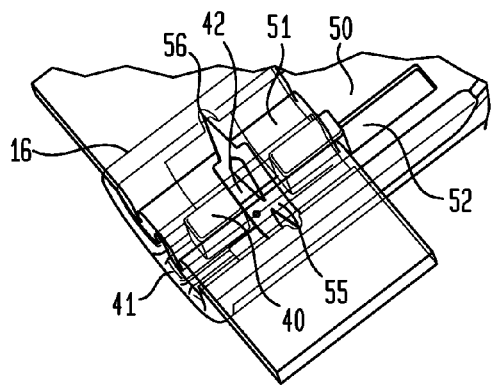
FIG. 10A is a view similar to FIG. 8A, but shown with the retaining arm in the retracted position.

The catheter assembly 12 further includes a retaining arm 50 (FIGS. 4A and 4B) disposed within the outer tube 16 and longitudinally slidable therein between an initial position (FIG. 8C) and a retracted position (FIG. 10A). The retaining arm 50 includes a pair of fingers 51 separated by an elongated slot 52. The slot 52 is sized to receive the anvil 40 when the retaining arm 50 is in the initial position shown in FIG. 8C. In this initial position, the fingers 51 lie on either side of the anvil 40 and engage a clip 55 disposed within the gap 42, holding it in place against the closed side of 41 of the outer tube 16. The retraction of the retaining arm 50 releases the clip 55 for application to tissue.

The clip 55 (FIG. 10A) may be made of a memory metal and may be biased to curl into a substantially round configuration (FIG. 10B) when the retaining arm 50 is retracted proximally and the fingers 51 no longer overlie the clip. A prong 56 at each end of the clip 55 is adapted to become embedded in the leaflet tissue when the clip is deployed.

Figure 2B:
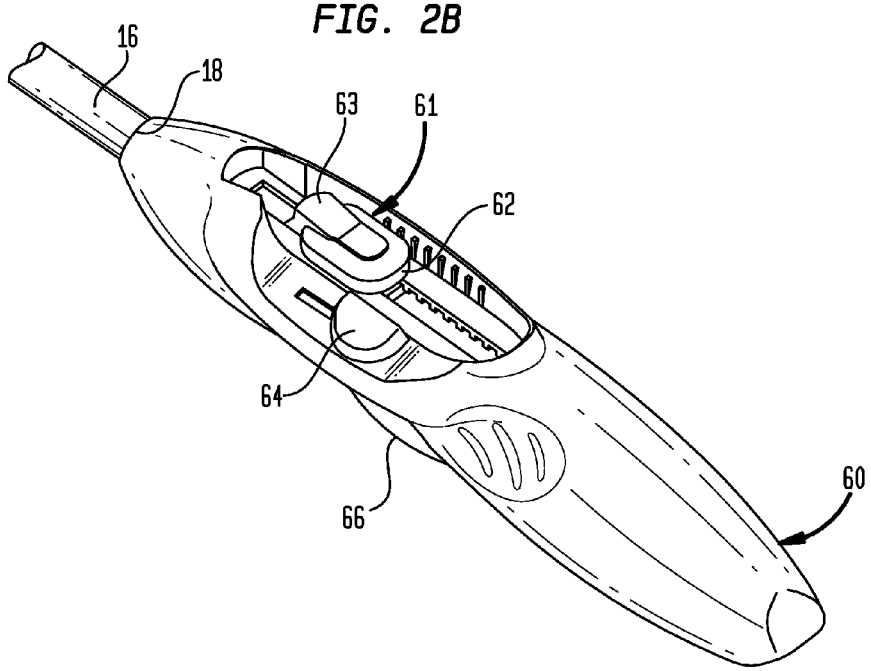
FIGS. 2B and 2C are a perspective view and a longitudinal cross-sectional view of one embodiment of a handle suitable for controlling the device of FIG. 2A, shown with the buttons positioned to correspond to the positions of the components of the device shown in FIG. 2A.
Figure 2C:
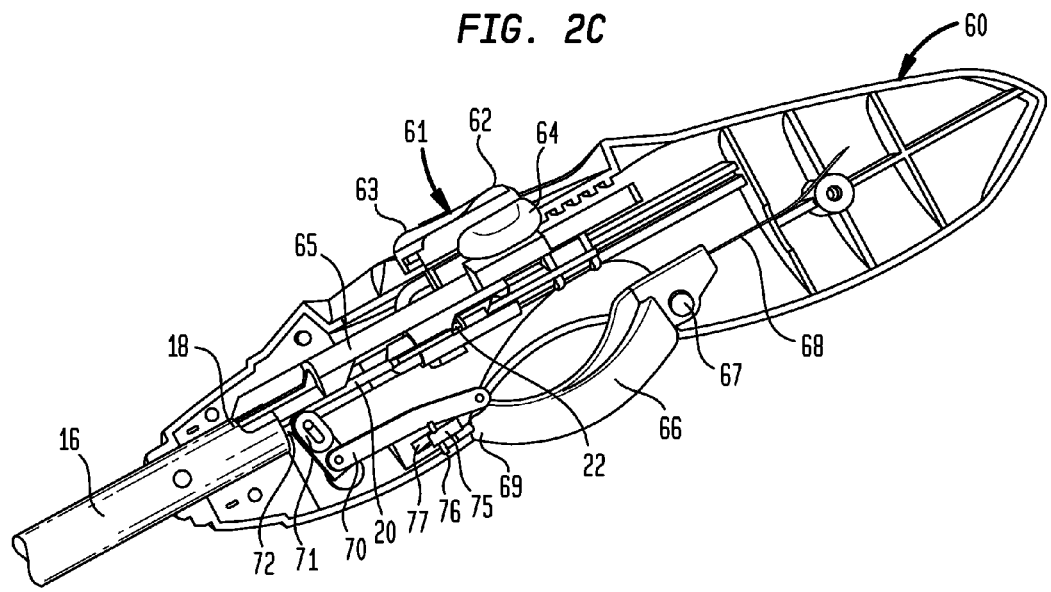

Referring now to FIGS. 2B and 2C, the device 10 further includes a handle 60 at the proximal end 18 of the outer tube 16. The handle 60 includes a first button 61, a second button 64, and a third button 66 for controlling the operation of the containment tube 20, the grasping wire 22, the fork 30, and the retaining arm 50. The first button 61 has a first portion 62 and a second portion 63 that are moveable longitudinally relative to the handle 60 and relative to one another. The first portion 62 is attached to the containment tube 20, such that sliding movement of the first portion in a proximal or distal direction results in a corresponding sliding movement of the containment tube. The second portion 63 is attached to the grasping wire 22, such that sliding movement of the second portion in a proximal or distal direction results in a corresponding sliding movement of the grasping wire. The containment tube 20 and the grasping wire 22 may be moved together by the simultaneous movement of the first and second portions of the button 61. Alternatively, the containment tube 20 and the grasping wire 22 may be moved independently of one another by moving one of the portions of the button 61 while the other portion remains stationary. For example, sliding the second portion 62 distally while the first portion 63 remains stationary advances the grasping wire 22 out from the containment tube 20, resulting in deployment of the hook 24.

The second button 64 is moveable longitudinally relative to the handle 60 for controlling the movement of the fork 30 relative to the outer tube 16. The second button 64 is attached to one end of a linkage 65, the other end of which is attached to a coupling block 37 (FIG. 4B) positioned in the distal portion 14 of the catheter assembly 16. The coupling block 37, in turn, is coupled to the fork 30 via a pivot pin 38 and a spring 39 that extends between the fork and the coupling block. The spring 39 is biased to rotate the fork 30 about the pivot pin 38 so that the tines 31 of the fork move laterally away from the closed side 41 of the outer tube 16.

The third button 66 has a trigger shape and is connected at one end to the handle 60 by a pivot pin 67 that allows for movement of the button in a lateral direction relative to the longitudinal axis of the handle for controlling the movement of the retaining arm 50 relative to the outer tube 16. A spring 68 biases the third button 66 to return to its initial position (FIG. 2C) after the button has been actuated (FIG. 10D). The opposite end 69 of the third button 66 is pivotally coupled to a linkage assembly including a first linkage 70, a second linkage 71, and a third linkage 72, all of which are pivotally connected to one another in series. The third linkage 72 is attached to a coupling block positioned in the distal portion 14 of the catheter assembly 12. The coupling block 53, in turn, is attached to a proximal end 54 (FIG. 4B) of the retaining arm 50, such that actuation of the third button 66 may cause the third linkage 72 to slide proximally to retract the retaining arm and thereby deploy the clip 55 (FIG. 10B).

Referring again to FIGS. 2B and 2C, a safety catch 75 may be connected to the handle 60 by a pivot pin 76, such that the safety catch may rotate between a locked position (FIGS. 8D and 8E) that prevents actuation of the third button 66 and an unlocked position (FIG. 10D) that frees the third button for actuation.

Figure 10B:
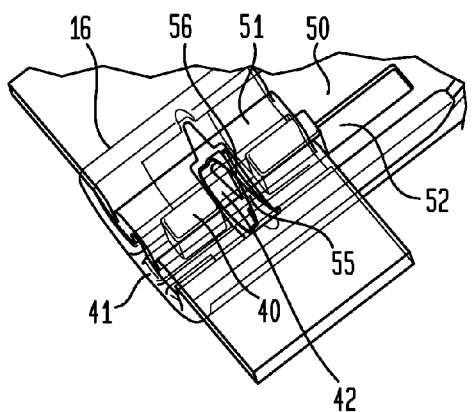
FIG. 10B is a view similar to FIG. 8A, but shown with the clip in a partially-deployed position.

To use the device 10 for transcatheter gathering of heart valve leaflet tissue, a user may first actuate the third button 66 of the handle 60 to retract the fingers 51 of the retaining arm 50 proximally of the gap 42 between the anvil portions 40a and 40b (FIG. 10B). A clip 55 may then be loaded into the gap 42, and the third button 66 released. The spring 68 will then bias the third button 66 back to its initial position, whereupon the retaining arm 50 will slide distally until the fingers 51 thereof cover the clip 55 and hold it in place.

Next, referring to FIG. 2A, the distal portion 14 of the catheter assembly 12 may be inserted into a patient through the apex of the heart, for example, into the left ventricle, so that the distal portion extends between the posterior leaflet 2 and the anterior leaflet 3 of the mitral valve 1. As shown in FIG. 2A, the distal edge 17 of the outer tube 16 may be disposed approximately at the coaption line 5 of the mitral valve 1, with the open side of the outer tube 16 facing the posterior leaflet 2 (alternatively, if the anterior leaflet 3 is being repaired, the open side of the outer tube may face the anterior leaflet). In a particular embodiment, the distal edge 17 of the outer tube 16 may be guided to a position at the coaption line 5 using the assistance of three-dimensional echocardiography to visualize the outer tube or other components of the catheter assembly 12.

Then, referring to FIG. 3, the containment tube 20 may be deployed by sliding the first and second portions 62 and 63 of the first button 61 together distally from an initial position (shown in FIG. 2B) to a deployed position. The distal movement of the first button 61 moves the tip 21 of the containment tube 20 beyond the distal end 17 of the outer tube 16, such that the tip 21 extends above the coaption line 5.

Figure 4C:
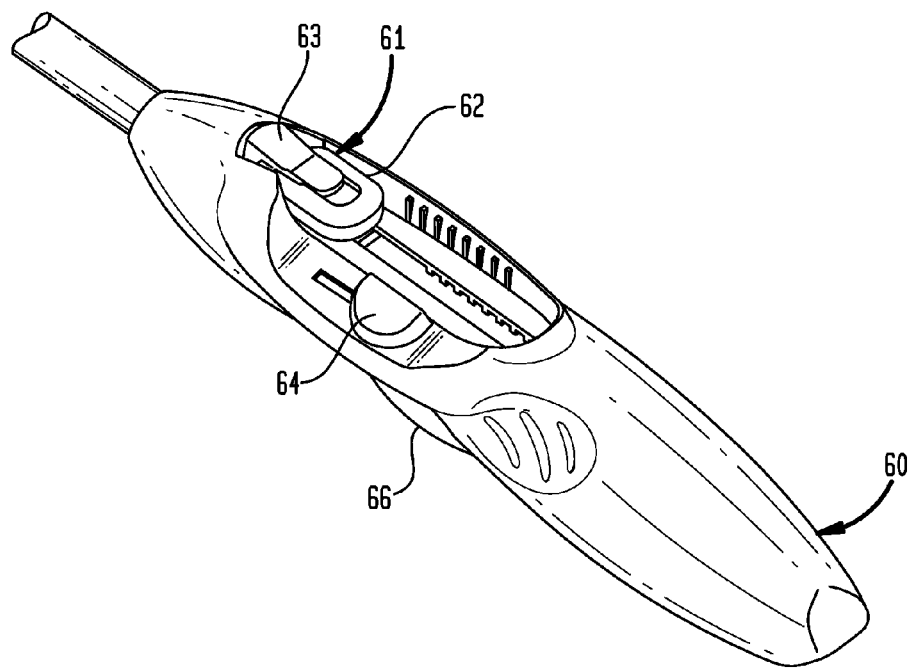
FIGS. 4C and 4D are a perspective view and a longitudinal cross-sectional view of the handle of FIG. 2B, shown with the buttons positioned to correspond to the positions of the components of the device shown in FIG. 4A.
Figure 4D:
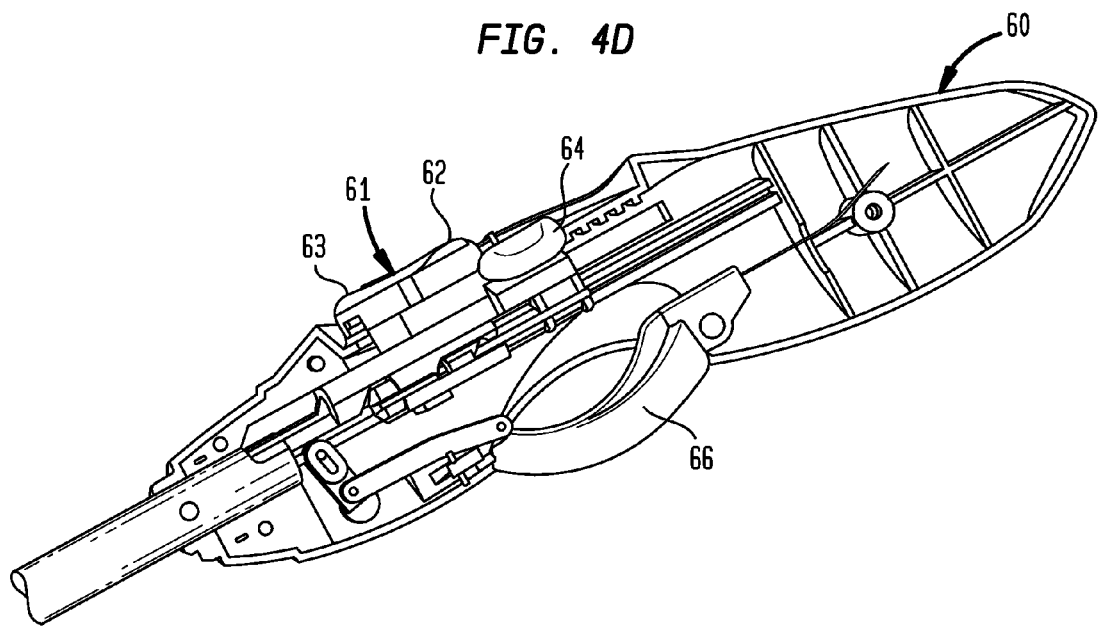

Referring to FIGS. 4A and 4B, the hook 24 may then be deployed to an extended position by sliding the second portion 63 of the first button 61 distally relative to the first portion 62 from an initial position (shown in FIG. 2B) to a deployed position (shown in FIGS. 4C and 4D). The distal movement of the second portion 63 relative to the first portion 62 moves the distal portion 23 of the grasping wire 22 out of the containment tube 20. No longer being constrained by the containment tube 20, the distal portion 23 of the grasping wire 22 may assume the curved shape of the hook 24.

Figure 5A:
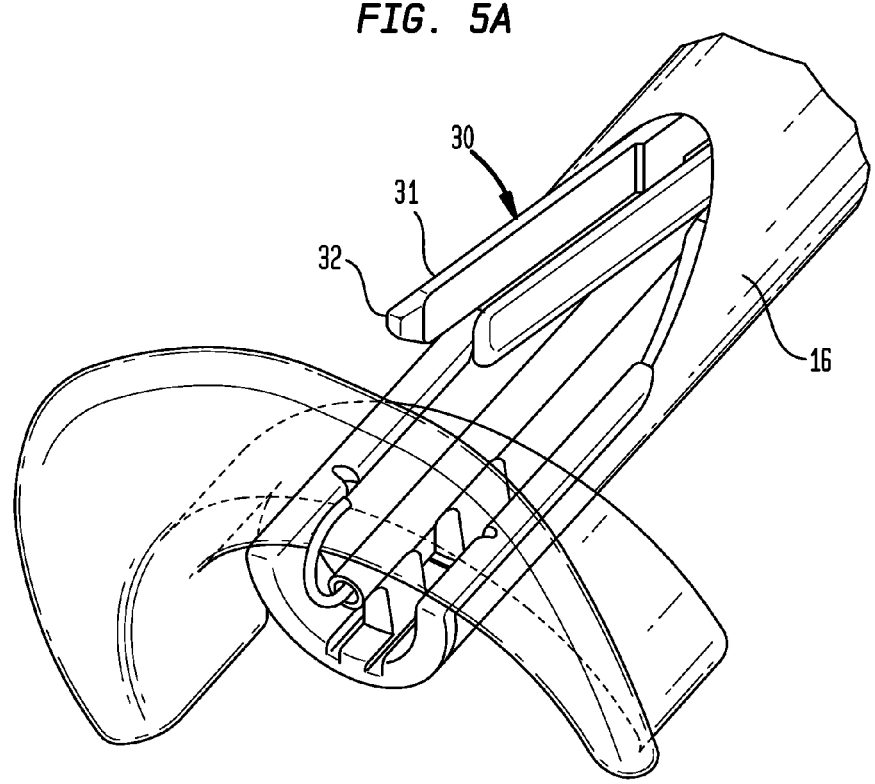
FIGS. 5A and 5B are a perspective view and a longitudinal cross-sectional view of the distal portion of the device of FIG. 2A, shown with the fork partially deployed.
Figure 5B:
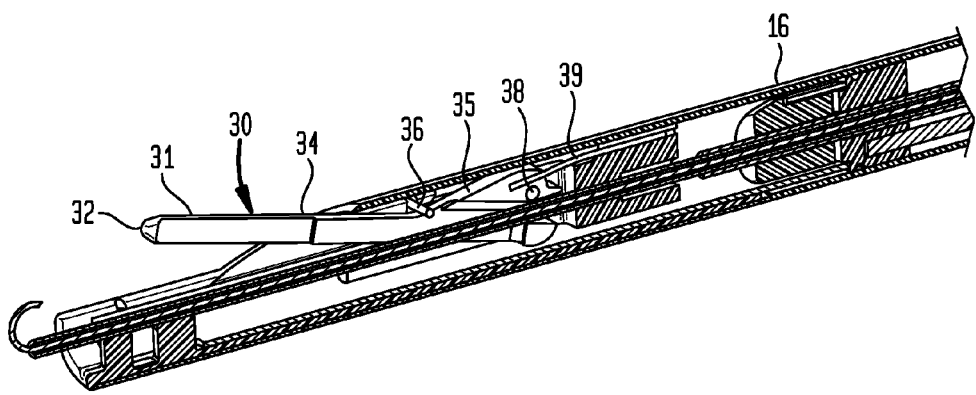

The fork 30 may then be partially deployed by sliding the second button 64 distally from an initial position (shown in FIG. 4C) to an intermediate position (not shown). As shown in FIGS. 5A and 5B, the distal movement of the second button 64 moves the fork 30 distally relative to the outer tube 16. As the fork 30 moves distally, the spring 39 will continue to exert a rotational force to the fork (in the clockwise direction of FIG. 5B), forcing the first cam surface 34 of each tine 31 against the pin 36. The distal movement of the cam surface 34 against the pin 36 will allow the ends 32 of the tines 31 to move gradually away from the closed side 41 of the outer tube 16 and away from the anvil 40.

Figure 6A:
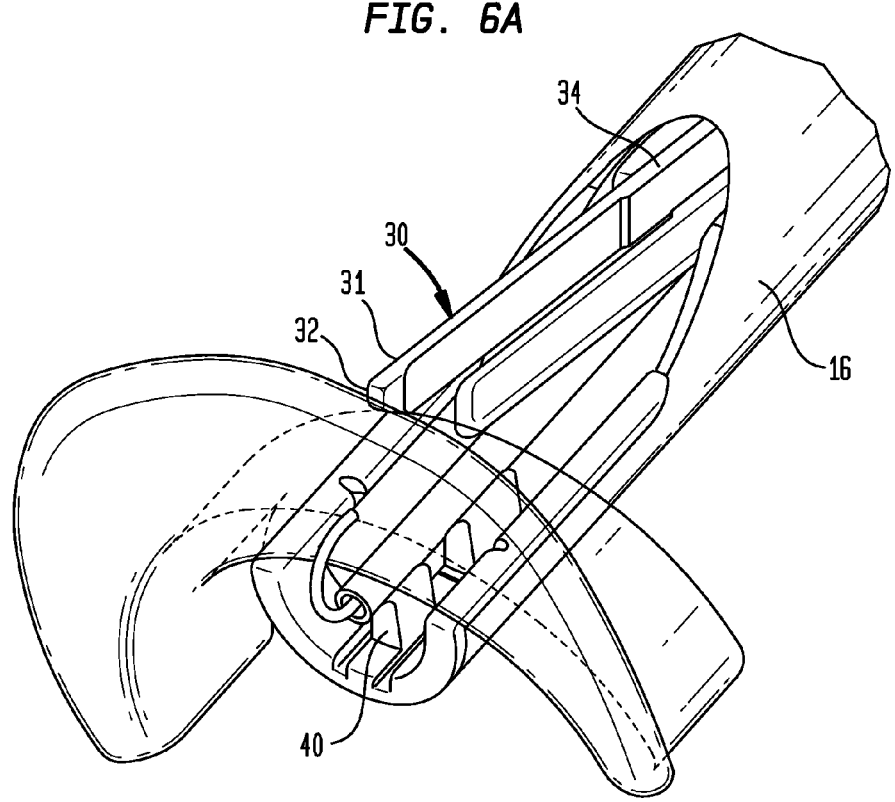
FIGS. 6A and 6B are a perspective view and a longitudinal cross-sectional view of the distal portion of the device of FIG. 2A, shown with the fork in the support position.
Figure 6B:
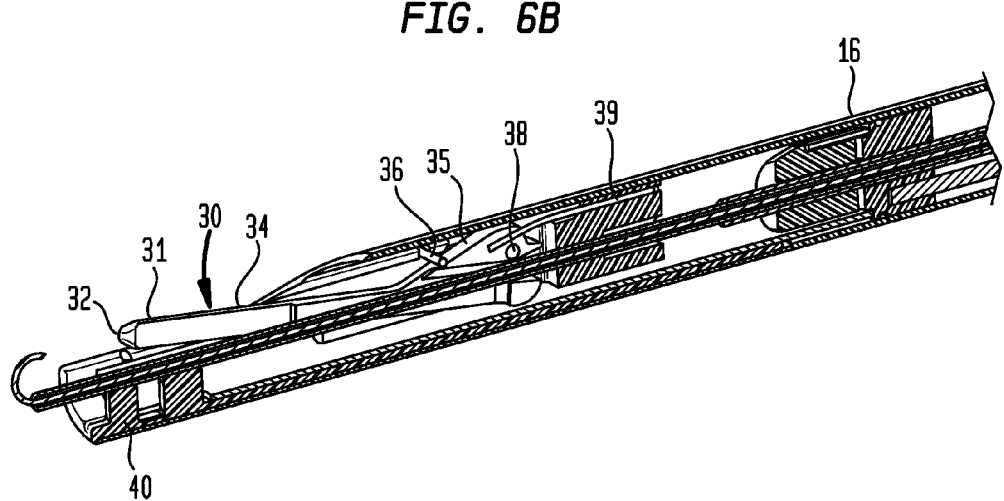
Figure 6C:
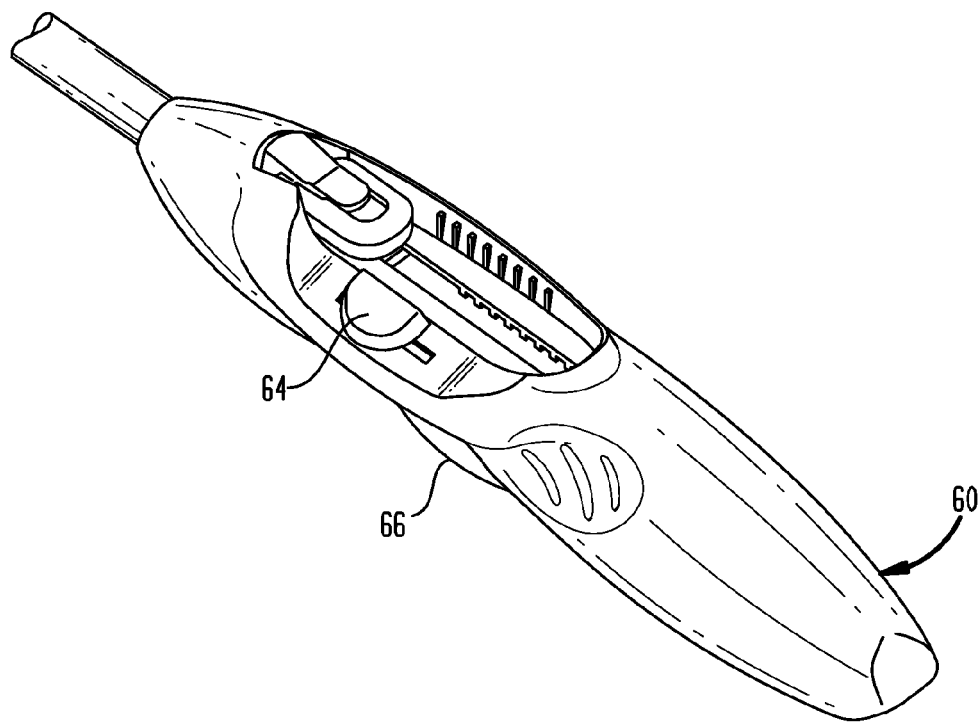
FIGS. 6C and 6D are a perspective view and a longitudinal cross-sectional view of the handle of FIG. 2B, shown with the buttons positioned to correspond to the positions of the components of the device shown in FIG. 6A.
Figure 6D:
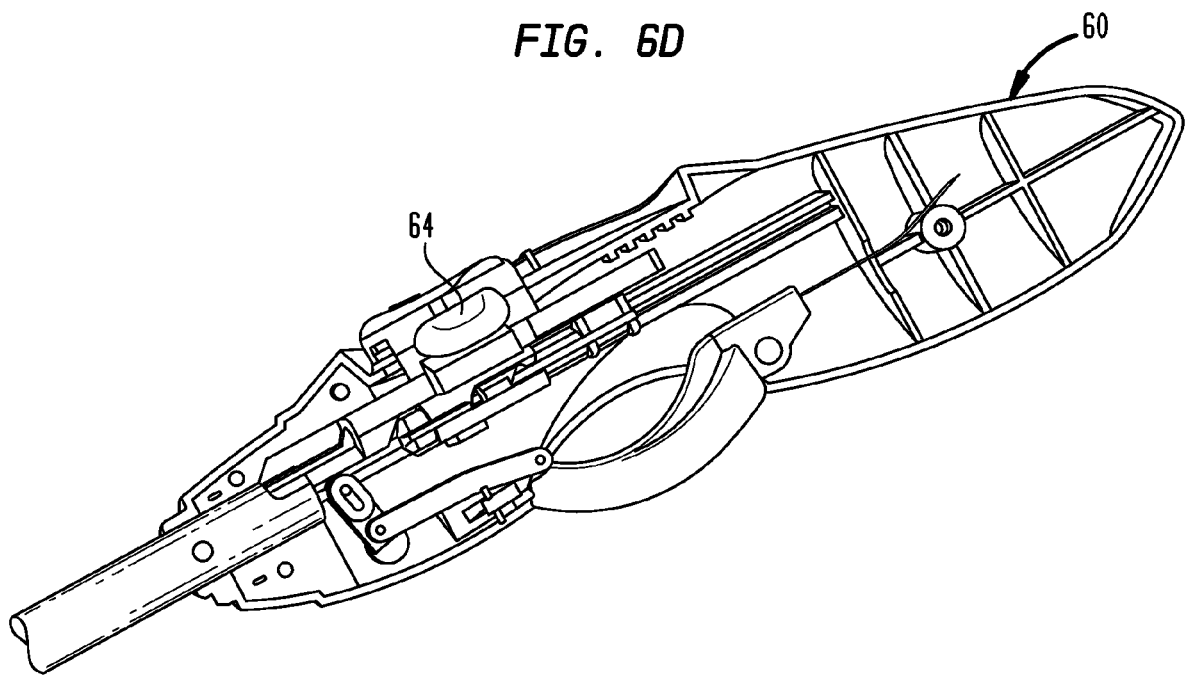

The fork 30 may continue to be deployed toward an open position by further movement of the second button 64 in the distal direction. As the fork 30 advances, the ends 32 of the tines 31 will continue to move laterally away from the closed side 41 of the outer tube 16 until the pin 36 reaches the intersection of the cam surfaces 34 and 35. Because the cam surface 35 is at a different angle than the cam surface 34, the interaction of the pin 36 and the cam surface 35 will exert a rotational force in the opposite direction as the fork 30 continues to advance. That is, as the fork 30 moves further distally, the pin 36 will exert a downward force tending to rotate the fork in the opposite direction (i.e., counterclockwise in FIG. 6B). As this latter force is greater than the rotation force exerted by spring 39, further distal movement of the fork 30 will cause the ends 32 of the tines 31 to move laterally towards the closed side 41 of the outer tube 16 and towards the anvil 40.

Figure 7A:
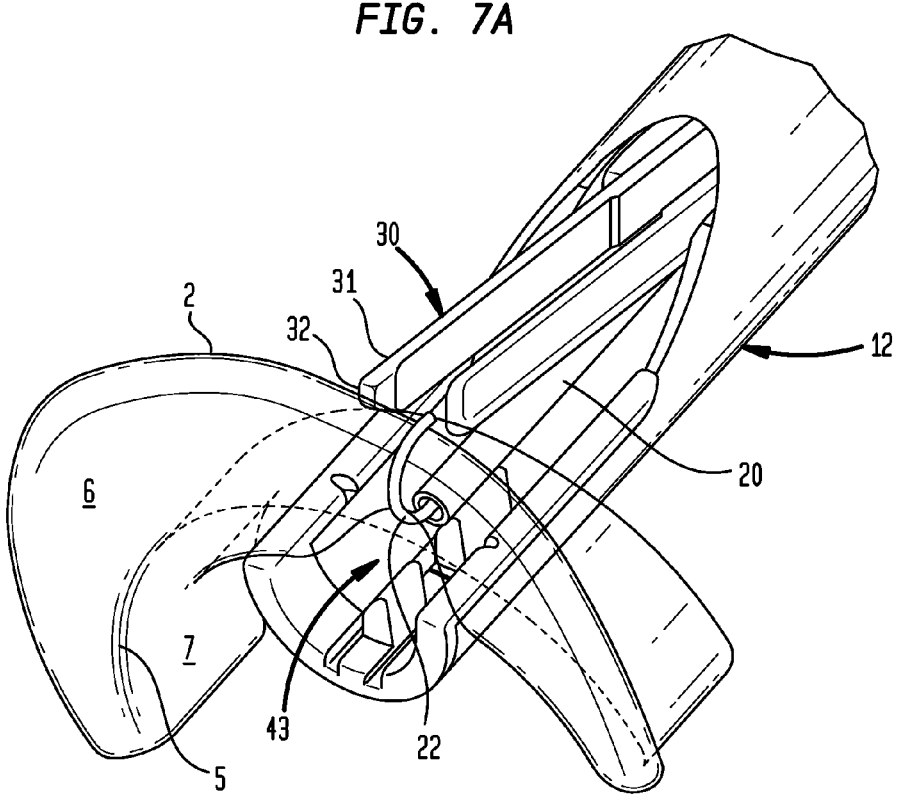
FIG. 7A is a perspective view of the distal portion of the device of FIG. 2A, shown with the hook in the partially-retracted position and the fork in the support position.
Figure 7B:
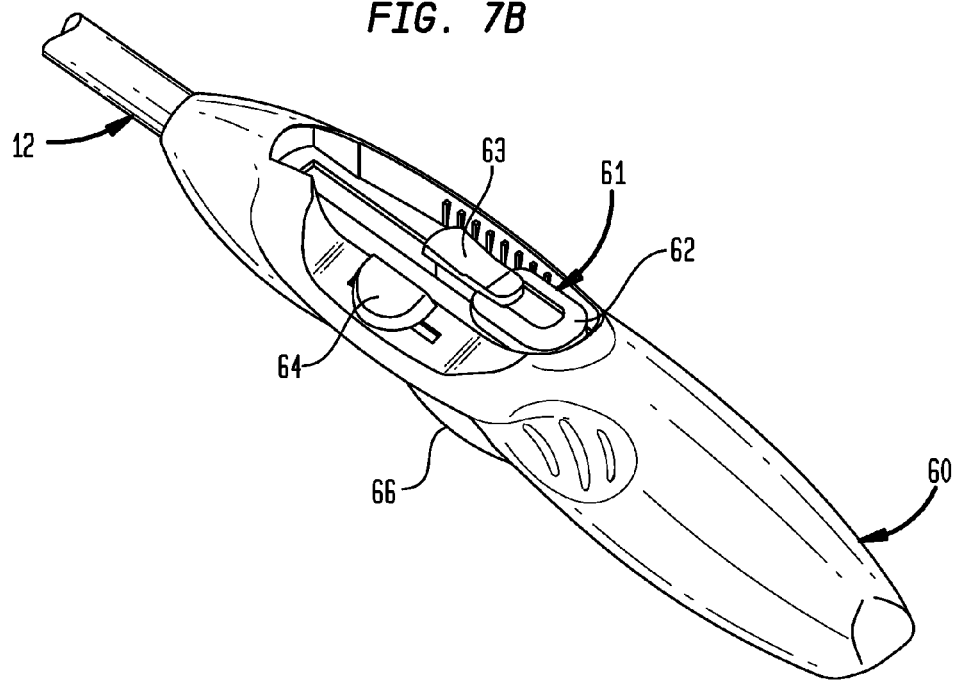
FIG. 7B is a perspective view of the handle of FIG. 2B, shown with the buttons positioned to correspond to the positions of the components of the device shown in FIG. 7A.

Referring to FIGS. 7A and 7B, the hook 24 may be partially retracted against the tissue of the posterior leaflet 2 by sliding the first and second portions 62 and 63 of the first button 61 together proximally (FIG. 7B). The proximal movement of the first button 61 partially retracts both the containment tube 20 and the grasping wire 22, such that the hook 24 engages against the upper surface 6 of the posterior leaflet 2 and pulls tissue of the leaflet into the space 43 between the containment tube and the tines 31 of the fork 30.

Figure 10C:
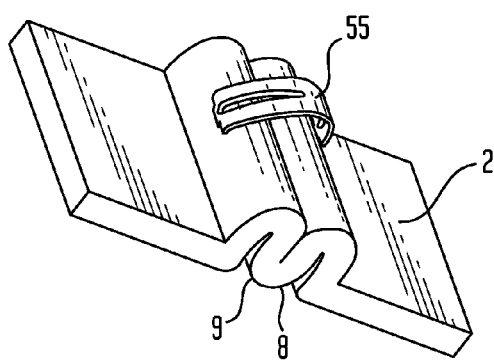
FIG. 10C is a diagrammatic view of the clip and the posterior mitral valve leaflet of FIG. 10B, shown with the clip in a partially-deployed position.
Figure 10D:
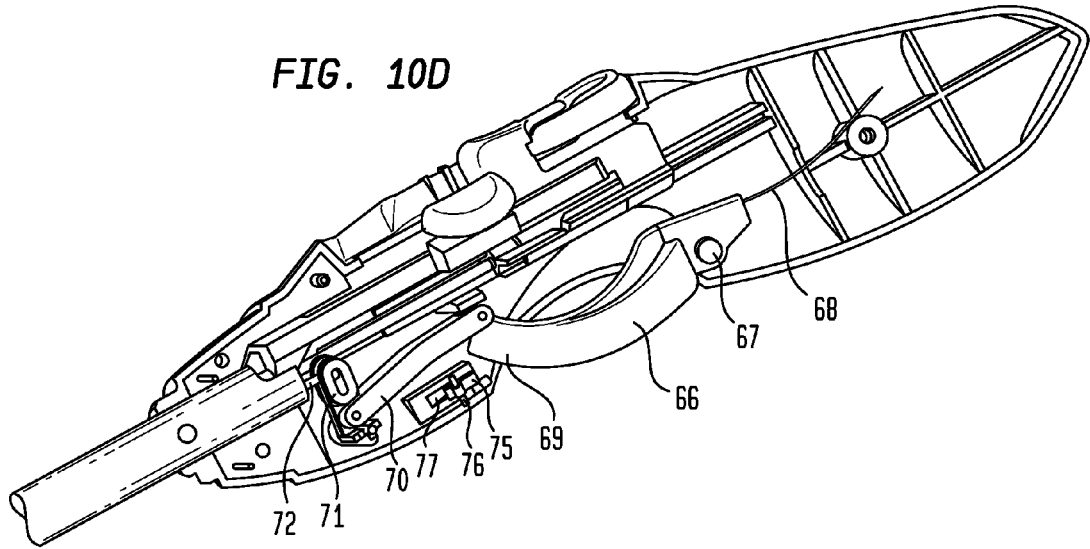
FIG. 10D is a longitudinal cross-sectional view of the handle of FIG. 2B, shown with the buttons positioned to correspond to the positions of the components of the device shown in FIG. 10A.

The tissue captured in the space 43 may be clamped between the anvil 40 and the tines 31 of the fork 30 by further sliding of the second button 64 distally to the fully deployed position. The further distal movement of the second button 64 moves the fork 30 further distally relative to the outer tube 16. As the fork 30 advances further toward a closed position adjacent the anvil 40, the interaction of the second cam surface 35 with the pin 36 will force the tines 31 of the fork toward the anvil and the closed side 41 of the outer tube 16, squeezing the captured tissue 9 therebetween. Continued movement of the fork 30 toward the anvil 40 will force the captured tissue 9 into the space 33 between the tines 31, and into the spaces between the tines and the closed side 41 of the outer portion 16. A W-shaped pleat 8 (FIG. 10C) will thus be formed in the captured tissue 9, with the raised center portion of the W overlying the anvil 40, and the two lower portions of the W lying between the tines 31 and the closed side 41 of the outer tube 16. By forming a W-shaped pleat 8, most or all of the portion of the posterior leaflet 2 that is billowed, loose, or floppy may be gathered and tightened.

With the tissue captured, the retaining arm 50 may be retracted by releasing the catch 75 and actuating the third button 66 by depressing it toward the handle 60. The retaining arm 50 may be retracted until the fingers 51 thereof are proximal of the gap 42 in the anvil 40 (FIG. 10B). At this juncture, the fingers 51 will no longer overlie the clip 55, such that the two prongs 56 of the clip will be free to spring away from the closed surface 41 of the outer tube 16 and become embedded in the captured tissue 9 of the posterior leaflet 2, thereby securing the tissue in the pleated form.

At this point, the clip 55 may be only partially engaged into the posterior leaflet 2 because the tines 31 of the fork 30 are positioned within the folds of the pleat 8. In a particular example, the clip 55 may be engaged in the lower portion 7 of the posterior leaflet 2 close to the coaption line 5. Optionally, a suture, such as the suture 258 described below with respect to FIGS. 16A and 16B, may extend from the clip 55 to the catheter assembly 12 so that the clip may be retrieved using the device 10, for example, if the clip has been installed at a sub-optimal location in the posterior leaflet 2 or does not become adequately embedded in the tissue. A user may desire to disengage the clip from the tissue and deploy another one.

After the clip 55 has been adequately secured in the tissue of the posterior leaflet 2, the device 10 may be withdrawn from the patient. To withdraw the device 10, the hook 24 may first be withdrawn from engagement with the posterior leaflet 2 by retracting the second portion 63 of the first button 61 relative to the first portion 62 thereof. This action causes the hook 24 to straighten as the grasping wire 22 retracts into the containment tube 20.

Figure 8B:
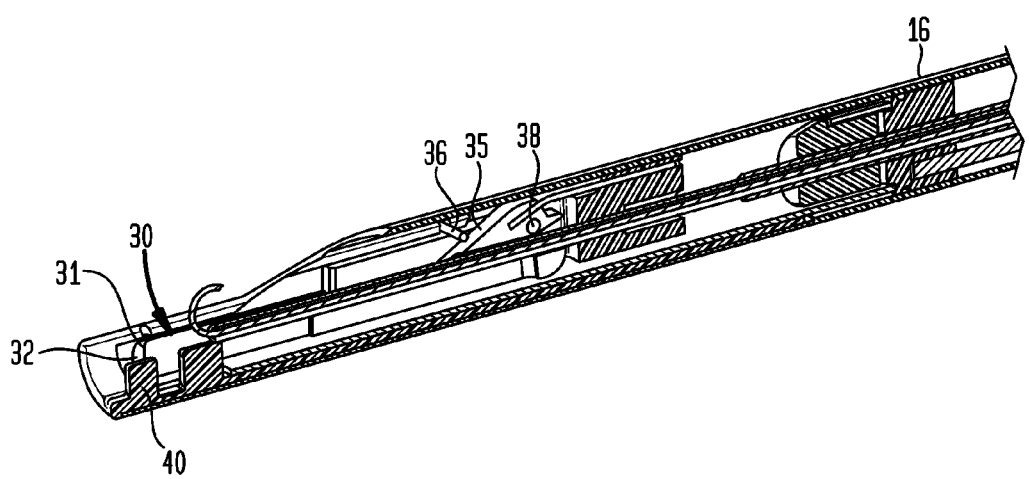

Next, the fork 30 may be withdrawn from within the clip 55. To withdraw the fork 30, the second button 64 may be moved proximally, thereby moving the fork proximally relative to the outer tube 16. While the fork 30 moves proximally, the spring 39 will exert a rotational force to the fork (in the clockwise direction of FIG. 8B), forcing the second cam surface 35 against the pin 36. The proximal movement of the cam surface 35 against the pin 36 will allow the ends 32 of the tines 31 to move gradually away from the closed side 41 of the outer tube 16 and away from the anvil 40. As the fork 30 continues to move proximally, the ends 32 of the tines 31 will continue to move laterally away from the closed side 41 of the outer tube 16 until the pin 36 reaches the intersection of the cam surfaces 34 and 35. Because the cam surface 35 is at a different angle than the cam surfaces 34, the interaction of the pin 36 and the cam surfaces 34 will exert a rotational force in the opposite direction as the fork 30 continues to move proximally. That is, as the fork 30 moves further proximally, the pin 36 will exert a downward force tending to rotate the fork in the opposite direction (i.e., counterclockwise in FIG. 5B). As this latter force is greater than the rotation force exerted by spring 39, further proximal movement of the fork 30 will cause the ends 32 of the tines 31 to move laterally towards the closed side 41 of the outer tube 16, thereby enabling the fork 30 to retract into the outer tube.

Once the fork 30 has disengaged from within the clip 55, the two prongs 56 of the clip may become more tightly embedded in the posterior leaflet 2, such that the two prongs may cross one another, thereby allowing the clip to extend along an arc that is greater than 360 degrees. Finally, the catheter assembly 12 may be withdrawn from the patient through the apex of the heart. The procedure described above may be repeated to apply one or more additional clips 55 onto the same posterior leaflet 2.

Figure 11A:
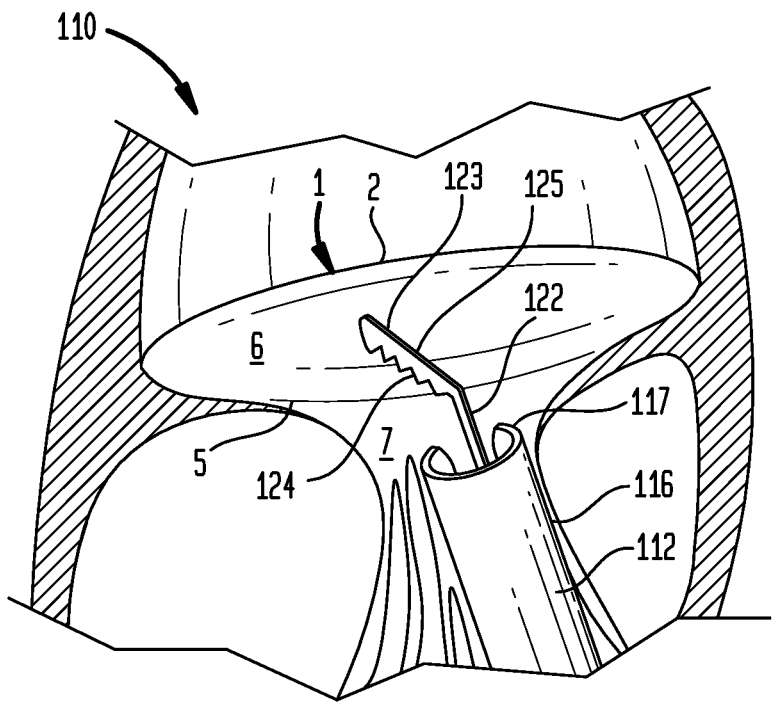
FIG. 11A is a diagrammatic view of the distal portion of another embodiment of a device for transcatheter gathering of heart valve leaflet tissue, shown engaged with the posterior leaflet of the mitral valve and with the grasping arm deployed.
Figure 11B:
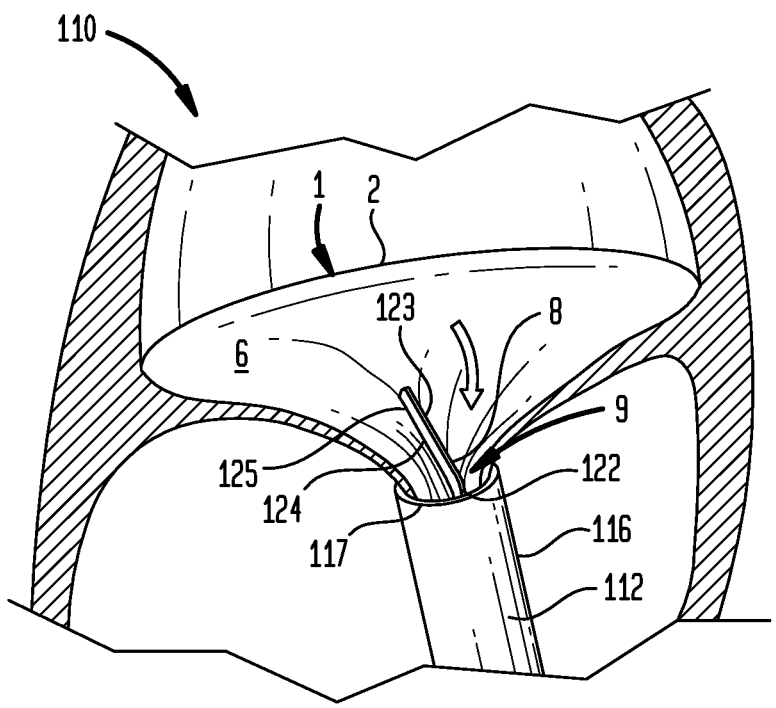
FIG. 11B is a diagrammatic view of the distal portion of the device of FIG. 11A, shown with the grasping arm in the partially-retracted position.
Figure 13E:
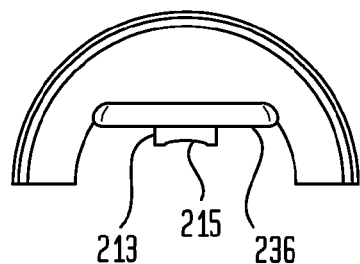
FIGS. 13E and 13F are a proximal end view and a distal end view respectively, of the component of FIG. 13A.
Figure 13F:
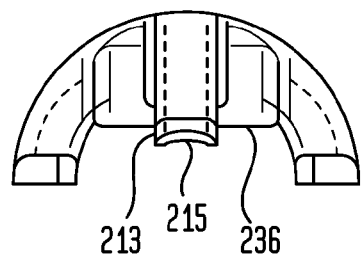
Figure 14A:
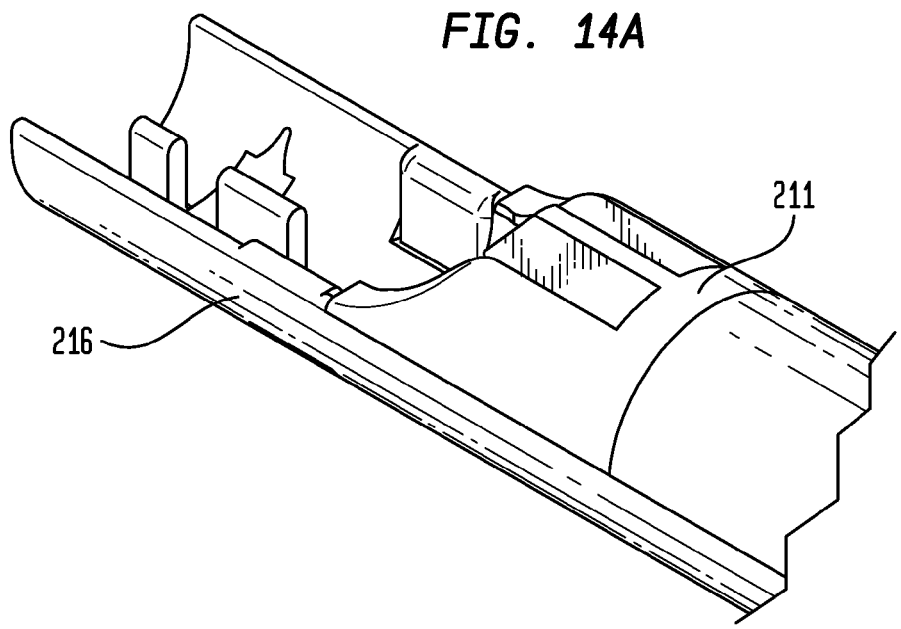
FIG. 14A is a perspective view of the outer tube of FIG. 12A assembled with the component of FIG. 13A.
Figure 14B:
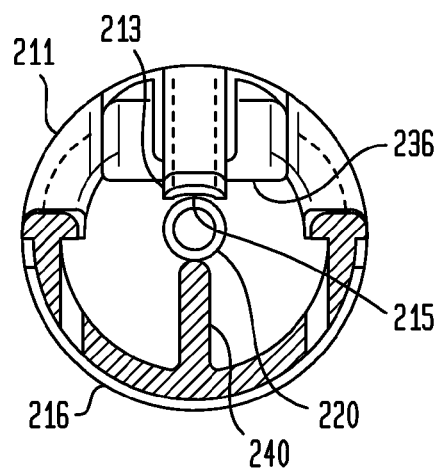
FIG. 14B is a lateral cross-sectional view of the assembly of FIG. 14A, showing the location of a containment tube such as that shown in FIG. 3.

An alternative embodiment of a device 110 for transcatheter gathering of heart valve leaflet tissue is shown in FIGS. 11A and 11B. The device 110 is similar to the device 10 described above, but includes an alternate hook arrangement. Rather than having a grasping wire whose distal end forms a hook shape when deployed from a containment tube, the device 110 has a grasping wire 122 whose distal end 123 has a substantially linear configuration when fully retracted within the outer tube 116, and that bends to form an arm 125 having a dog-leg configuration with the remainder of the grasping wire when deployed beyond the distal end 117 of the outer tube. That is, the grasping wire 122 may be formed from a memory metal or a strong, resilient metal or polymer that will cause the arm 125 to bend automatically when deployed. Serrations 124 may be formed on an edge of the arm 125 so as to confront the upper portion 6 of a posterior leaflet 2 of a mitral valve 1 in use.

The device 110 may be used for transcatheter gathering of heart valve leaflet tissue in a manner similar to the device 10 described above, and may be controlled by a handle similar to the handle 60 of FIG. 2B. The arm 125 of the grasping wire 122 may be deployed by moving the grasping wire distally relative to the outer tube 116 until the arm 125 lies beyond the distal edge 117 thereof, thereby freeing the arm to bend into the dog-leg configuration (FIG. 11A).

The remainder of the procedure for gathering and securing the tissue of the posterior leaflet 2 is substantially the same as the procedure described above in connection with the use of device 10. After a clip, such as the clip 55, has been secured to the posterior leaflet 2, the arm 125 may be disengaged from the posterior leaflet by first moving the grasping wire 122 distally relative to the outer tube 116 to disengage the serrated edge 124 from the leaflet tissue. Subsequently, the grasping wire 122 may be proximally withdrawn relative to the outer tube 116, with the arm 125 straightening as it retracts within the outer tube. With the arm 125 fully retracted, the device 110 may be withdrawn from the patient.

In a particular embodiment, the device 110 may include a containment tube (not shown) for the grasping wire 122, similar to the containment tube 20 of the device 10. In such an embodiment, the grasping wire 122 may have a substantially linear configuration when fully retracted within the containment tube and the dog-leg configuration when the arm 125 is deployed from the containment tube.

An alternative embodiment of a device 210 for transcatheter gathering of heart valve leaflet tissue is shown in FIGS. 12A through 16B. The device 210 is similar to the device 10 described above, but the device 210 includes an alternate outer tube and retaining arm arrangement. As shown in FIGS. 12A-12C, the device 210 has a tab 244 protruding radially inward from each open edge 245 of the closed side 241 of the outer tube 216. The two tabs 244 may act as a guide to prevent lateral movement of the distal end of the retaining arm 250 (FIG. 15A) away from the closed side 241 when the retaining arm moves longitudinally relative to the outer tube 216 to release a clip. Although the figures show one tab 244 protruding from each open edge 245, the open edge may include any number of tabs protruding therefrom to guide the distal end of the retaining arm 2500 and to prevent it from moving laterally.

Referring to FIGS. 13A-13F, the device 210 also includes a retainer 211 that may be assembled to the outer tube 216 near its distal end. The retainer 211 may have a pivot edge 236 having the same function as the pin 36 shown in FIG. 4B. Similar to the pin 36, the pivot edge 236 is orientated substantially orthogonal to the longitudinal direction of travel of a fork, such as the fork 30 shown in FIG. 4B, to control transverse movement of the fork relative to the outer tube 216.

The retainer 211 may also include a support element 213 having a curved contact surface 215 that cooperates with the anvil 240 to guide the longitudinal movement of the containment tube 220 and to prevent it from being displaced laterally during the process of gathering or releasing leaflet tissue. The anvil 240 may have a curved contact surface facing the curved contact surface 215 of the retainer 211 to further guide the containment tube 220. The curved contact surfaces of the retainer 211 and/or the anvil 240 may prevent the containment tube 220 from being displaced in any direction perpendicular to the longitudinal axis of the containment tube.

Figure 15A:
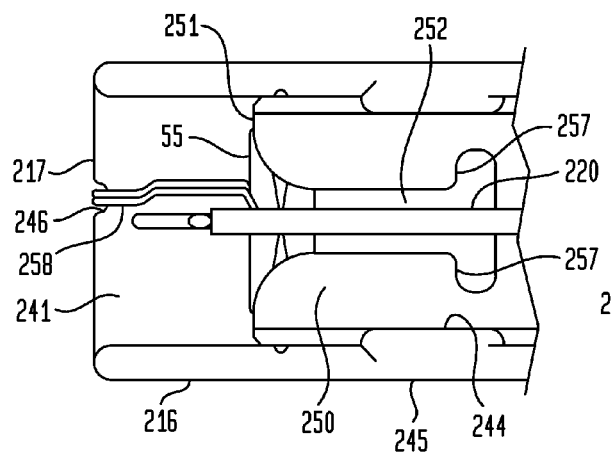
FIG. 15A is a top view of the outer tube of FIG. 12A, shown with a variant of the retaining arm of FIG. 8C.
Figure 15B:
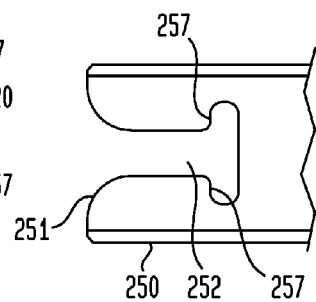
FIG. 15B is a top view of the retaining arm of FIG. 15A.
Figure 16A:
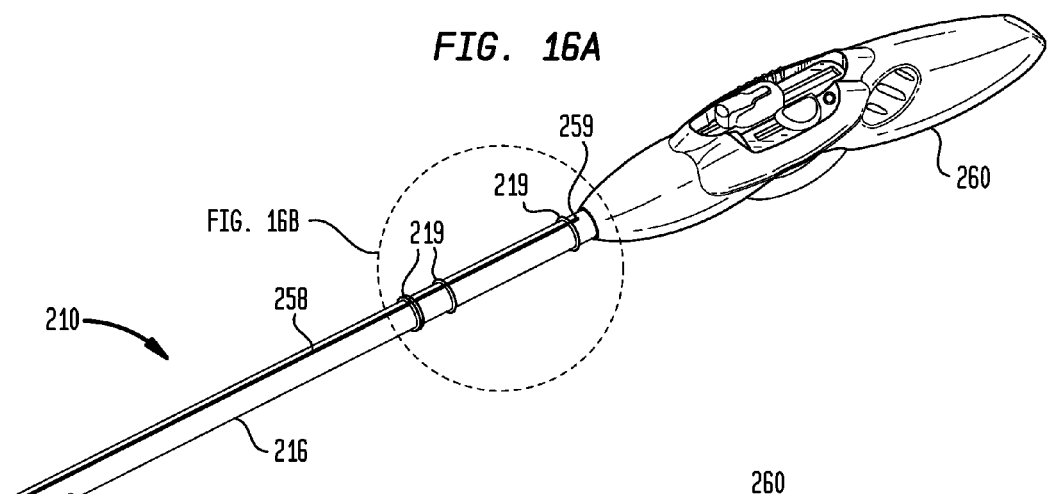
FIG. 16A is a perspective view of another embodiment of a device for transcatheter gathering of heart valve leaflet tissue.

Referring to FIGS. 15A and 15B, the retaining arm 250 of the device 210 is the same as the retaining arm 50 shown in FIG. 8C, except that the elongated slot 252 has a T-shaped opening at its proximal end. The T-shaped opening includes edges 257 facing in a proximal direction of the device. Such proximal-facing edges 257 may be advantageous when a user loads a clip 55 into the device 210. After a clip 55 has been loaded into the device, friction between the retaining arm 250 and the outer tube 216 and/or the clip may make it difficult for the user to slide the fingers 251 of the retaining arm over the clip simply through operation of the handle 260 (FIG. 16A). In such a situation, the user can grasp the edges 257 with a tool, such as a hook, and can manually pull the retaining arm 250 distally until the fingers 251 sufficiently cover the clip 55.

Figure 16B:
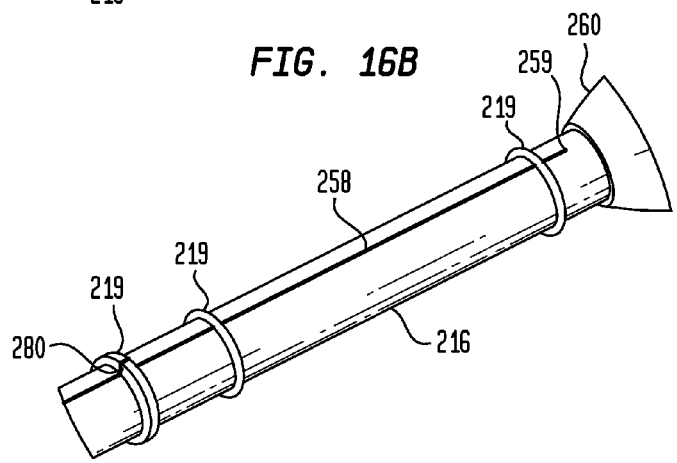
FIG. 16B is an enlarged view of a portion of the device of FIG. 16A including the suture retaining rings.

As shown in FIGS. 16A and 16B, the device 210 may include a suture 258 extending from the clip 55 to a position adjacent the handle 260 so that the clip may be retrieved using the device 210 after the clip has been released, for example, if the clip has been installed at a sub-optimal location in the posterior leaflet 2 or does not become adequately embedded in the tissue. The suture 258 may extend around the clip 55, over a notch 246 at the distal end of the outer tube 216, and along the exterior of the outer tube to one or more suture retaining rings 219. The device 210 may include three rings 219, or any number of rings greater or less than three. The suture 258 may wrap around one or more of the rings 219, and may extend through a hole 280 in one or more of the rings 219. The ends 259 of the suture 258 may be disposed near the handle 260 for grasping by the user.

In use, after the clip 55 has been released and the user wants to retrieve the clip from the leaflet tissue, the user may grasp both ends 259 of the suture 258 and pull until the clip is freed from the leaflet tissue. If the clip has been placed properly and is to remain in place in the leaflet tissue, the user may grasp only one end 259 of the suture 258 and pull the one end until the other end is pulled out of the clip, or the user may cut the suture near the clip 55 and pull the suture out by both of its ends.

Figure 17:
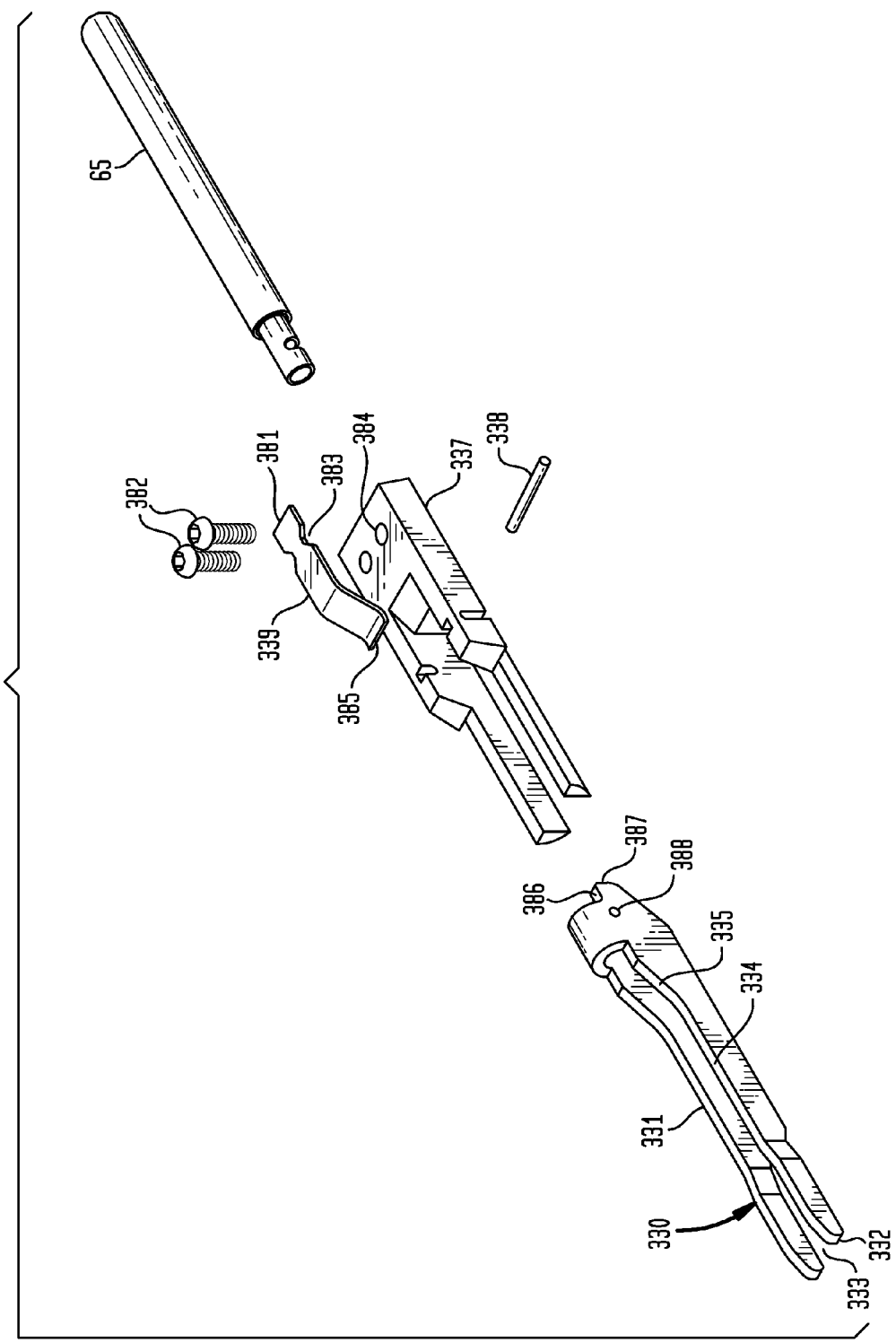
FIG. 17 is an exploded perspective view of a variant of the fork 30 shown in FIG. 4B.

Referring to FIG. 17, a fork 330 suitable for use in any of the devices described herein has the same function as the fork 30 shown in FIG. 4B, but the fork 330 may be made by bending a flat sheet of metal or other material, rather than by a molding process.

The fork 330 includes two tines 331 having respective ends 332, the tines being spaced apart from one another by an internal gap 333. The fork 330 further includes first cam surfaces 334 that are the top surfaces of the tines 331 and second cam surfaces 335 located proximally of the tines. The linkage 65 extends between the control handle, such as the handle 60 or 260 described above, and a coupling block 337, so that they are actuating members on the handle can control the movement of the fork 330 relative to the outer tube of the device. The coupling block 337, in turn, is coupled to the fork 330 via a pivot pin 338 and a spring 339 that extends between the fork and the coupling block. The spring 339 is biased to rotate the fork 330 about the pivot pin 338 in the same manner as has been described above with reference to the movement of the fork 30.

The proximal end 381 of the spring 339 may be attached to the coupling block 337 by two screws 382 that extend through notches 383 in the spring and into tapped holes 384 in the coupling block. The distal end 385 of the spring 339 is configured to apply a force to a surface 386 on the fork 330 located between the proximal end 387 of the fork and an opening 388 adapted to receive the pin 338. As a result of this arrangement, the force applied by the spring will tend to rotate the fork 330 about the pin 338.

In the devices shown in the figures, particular structures are shown that are adapted to gather, secure, and repair heart valve leaflet tissue. The invention also contemplates the use of any alternative structures for such purposes, including structures having different lengths, shapes, and configurations. For example, although the capture tool is shown in the form of a grasping wire 22 or 122, the capture tool may take other forms, including for example, a pincer-like structure such as a clamp. Although the clamping member is shown in the form of a fork 30, the clamping member may have other configurations, such as an arm having a curved surface such that outer edges of the arm can serve as tines, a lattice structure, or any other structure capable of retaining leaflet tissue against the anvil 40 and the closed surface 41 of the outer shaft 16. The tissue support is shown as an anvil 40, but may take other forms, such as a corrugated surface, a set of pins extending from the closed surface 41 of the outer shaft 16, or any other shape that can guide leaflet tissue into a desired shape onto which a clip 55 can be attached.

In another example, although the catheter assembly 12 is described as being controllable by the movement of a particular configuration of buttons 61, 64, and 66 of a handle 60, any mechanisms that are adapted to control the movement and deployment of the containment tube, grasping wire, fork, and clip may be used. Furthermore, although the grasping wires 22 and 122 are shown as having a hook 24 and a dog-leg arm 125, respectively, the distal portion of the grasping wire may have any shape or configuration that may be adapted to grasp a target portion of valve leaflet tissue and help to capture such tissue inside or adjacent the outer tube such that a clip may be applied to the captured tissue.

Moreover, although the fork 30 is described as having two tines 31 that cooperate with the anvil 40 to capture leaflet tissue and form same into a W-shaped pleat, the invention contemplates forks having any number of tines cooperating with any number of anvils to form any number of pleats in the captured tissue. For example, a fork having a single tine may cooperate with two anvils that are laterally spaced apart from one another to form leaflet tissue into a pleat. It will be appreciated that the more pleats that are formed, the more the tissue of the valve leaflet can be tightened. In a particular embodiment, the tissue capture mechanism may include an outer tube 16 without an anvil portion extending from the inner surface 41 of the outer tube, wherein the tines 31 of the fork 30 are adapted to capture leaflet tissue in a single contiguous space defined within the outer tube 16, such that a portion of the inner surface of the outer tube may serve as an anvil portion. In such an embodiment without an anvil portion extending from the inner surface 41 of the outer tube 16, the hook 24 and the containment tube 20 may serve as an anvil portion to cooperate with the fork 30 to form leaflet tissue into a W-shaped pleat.

Although the fork 30 is described as including cam surfaces 34 and 35 for controlling lateral movement of the tines 31 as the fork is moved distally and proximally relative to the outer tube 16, other mechanisms may be used for controlling such lateral movement of the tines. For example, cam surfaces located at any location along the fork may slide against any portion of the outer tube 16 or any surface projecting therefrom to control lateral movement of the tines. Alternatively, a mechanism controlled by a dedicated button of the handle may be used to actuate lateral movement of the tines relative to the outer tube 16.

Although the device 10 is shown as being adapted to apply a single clip 55 onto a posterior leaflet 2, the invention contemplates devices that are adapted to apply a plurality of clips to the leaflet tissue during a single insertion of the device into a patient. For example, the gap 42 between the anvil portions 40a and 40b may be sufficiently large to accommodate a plurality of clips 55 in side-by-side relationship. In such an embodiment, while leaflet tissue is captured within the outer tube 16, the retaining arm 50 may be retracted to a first position to apply a first clip 55 to the tissue at a first target location, and the retaining arm may then be further retracted to a second position to apply a second clip 55 to the tissue at a second target location spaced from the first location.

Although the various delivery devices have been described herein in connection with tightening the posterior leaflet of a mitral valve, all of the delivery devices may be used on other heart valve leaflets, such as the anterior leaflet of the mitral valve (which is shown in FIG. 1 as the anterior leaflet 3), or on any other tissue of the body for which a reduction in the length of the tissue would be beneficial.

Although the invention herein has been described with reference to particular embodiments in which the catheter assembly is inserted into the patient via an introducer and through the apex of the heart (i.e., transapical insertion), it is to be understood that the invention contemplates embodiments in which the catheter assembly extends through a portion of the vasculature of the patient to reach the heart, for example, through a transfemoral or subclavian artery. In such embodiments, some of the device components may have to be oriented in a different direction to that described herein. For example, the invention contemplates embodiments in which the distal portion of the catheter assembly approaches the mitral valve from the upstream side as well as from the downstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A transcatheter method of gathering tissue of a heart valve leaflet, the method comprising:
    inserting an elongated catheter assembly to a position adjacent the heart valve leaflet, the catheter assembly including a capture tool moveable between a retracted position and an extended position, a tissue support, and a clamping member moveable between an open position spaced from the tissue support and a closed position adjacent the tissue support;
    moving the capture tool from the retracted position to the extended position;
    moving the clamping member from an initial position to the open position adjacent the heart valve leaflet;
    manipulating the catheter assembly so that tissue of the heart valve leaflet is positioned between the tissue support and the clamping member;
    partially retracting the capture tool from the extended position toward the retracted position to gather an additional amount of tissue of the heart valve leaflet between the tissue support and the clamping member;
    moving the clamping member from the open position toward the closed position so as to clamp a substantial portion of the gathered tissue of the heart valve leaflet between the tissue support and the clamping member, the clamped tissue having a gathered configuration; and
    applying a clip from the catheter assembly to the clamped tissue so as to hold the clamped tissue substantially in the gathered configuration,
    wherein the gathered configuration includes a W-shaped pleat.

2. The method of claim 1, wherein a distal end of the capture tool has a hook shape.

3. The method of claim 1, wherein the capture tool extends in a longitudinal direction, and a distal end of the capture tool includes an arm extending in a direction transverse to the longitudinal direction, the arm having a serrated edge.

4. The method of claim 1, wherein the capture tool includes a grasping wire slideably disposed in a containment tube, the method further comprising sliding a distal portion of the grasping wire out from the containment tube so that the distal portion of the grasping wire changes from a linear shape to a hook shape.

5. The method of claim 4, wherein the grasping wire is made from a memory metal material.

6. The method of claim 1, wherein a distal portion of the clamping member has a fork shape.

7. The method of claim 1, wherein the catheter assembly extends in a longitudinal direction, and the tissue support includes first and second bodies spaced apart in the longitudinal direction.

8. The method of claim 1, wherein the catheter assembly further includes a retaining arm moveable between a distal position for retaining the clip and a proximal position for releasing the clip, and the step of applying the clip includes moving the retaining arm from the distal position to the proximal position, whereby the clip is released for application to the clamped tissue.

9. The method of claim 8, wherein the clip is biased from an open condition to a clamping condition and the retaining arm holds the clip in the open condition, and the step of moving the retaining arm from the distal position to the proximal position releases the clip for movement to the clamping condition.

10. The method of claim 1, wherein the catheter assembly further includes an operating handle having a first actuating member moveable in opposite longitudinal directions, and the step of moving the capture tool from the retracted position to the extended position includes moving the first actuating member in a first one of the longitudinal directions.

11. The method of claim 10, wherein the step of partially retracting the capture tool includes moving the first actuating member in a second one of the longitudinal directions opposite the first longitudinal direction.

12. The method of claim 10, wherein the operating handle includes a second actuating member moveable in the opposite longitudinal directions, and the step of moving the clamping member from the initial position to the open position includes moving the second actuating member in the first longitudinal direction.

13. The method of claim 12, wherein the step of moving the clamping member from the open position toward the closed position includes moving the second actuating member further in the first longitudinal direction.

14. The method of claim 10, wherein the operating handle includes a third actuating member moveable in a direction transverse to the longitudinal directions, and the step of applying the clip includes moving the third actuating member in the direction transverse to the longitudinal directions.

15. A transcatheter method of gathering tissue of a heart valve leaflet, the method comprising:
    inserting an elongated catheter assembly to a position adjacent the heart valve leaflet, the catheter assembly including a capture tool moveable between a retracted position and an extended position, a tissue support, and a clamping member moveable between an open position spaced from the tissue support and a closed position adjacent the tissue support;
    moving the capture tool from the retracted position to the extended position;
    moving the clamping member from an initial position to the open position adjacent the heart valve leaflet;
    manipulating the catheter assembly so that tissue of the heart valve leaflet is positioned between the tissue support and the clamping member;
    partially retracting the capture tool from the extended position toward the retracted position to gather an additional amount of tissue of the heart valve leaflet between the tissue support and the clamping member;
    moving the clamping member from the open position toward the closed position so as to clamp a substantial portion of the gathered tissue of the heart valve leaflet between the tissue support and the clamping member, the clamped tissue having a gathered configuration; and
    applying a clip from the catheter assembly to the clamped tissue so as to hold the clamped tissue substantially in the gathered configuration, wherein the catheter assembly extends in a longitudinal direction, and the step of moving the clamping member from the initial position to the open position includes moving a distal portion of the clamping member distally in the longitudinal direction and laterally away from the tissue support in a direction transverse to the longitudinal direction.

16. The method of claim 15, wherein the step of moving the clamping member from the open position toward the closed position includes moving the distal portion of the clamping member further distally in the longitudinal direction and laterally toward the tissue support in a direction transverse to the longitudinal direction.

17. The method of claim 16, wherein the step of moving the clamping member from the initial position to the open position includes sliding a first cam surface of the clamping member against a guide surface fixed relative to the catheter assembly to cause the distal portion of the clamping member to move laterally away from the tissue support, and the step of moving the clamping member from the open position toward the closed position includes sliding a second cam surface of the clamping member against the guide surface to cause the distal portion of the clamping member to move laterally toward the tissue support.

18. The method of claim 15, wherein the gathered configuration includes a W-shaped pleat.

19. A transcatheter method of gathering tissue of a heart valve leaflet, the method comprising:
   inserting an elongated catheter assembly to a position adjacent the heart valve leaflet, the catheter assembly including a capture tool moveable between a retracted position and an extended position, a tissue support, and a clamping member moveable between an open position spaced from the tissue support and a closed position adjacent the tissue support;
   moving the capture tool from the retracted position to the extended position;
   moving the clamping member from an initial position to the open position adjacent the heart valve leaflet;
   manipulating the catheter assembly so that tissue of the heart valve leaflet is positioned between the tissue support and the clamping member;
   partially retracting the capture tool from the extended position toward the retracted position to gather an additional amount of tissue of the heart valve leaflet between the tissue support and the clamping member;
   moving the clamping member from the open position toward the closed position so as to clamp a substantial portion of the gathered tissue of the heart valve leaflet between the tissue support and the clamping member, the clamped tissue having a gathered configuration; and
   applying a clip from the catheter assembly to the clamped tissue so as to hold the clamped tissue substantially in the gathered configuration,
   wherein the catheter assembly further includes an operating handle having a first actuating member moveable in opposite longitudinal directions, and the step of moving the capture tool from the retracted position to the extended position includes moving the first actuating member in a first one of the longitudinal directions, and
   wherein the capture tool includes a grasping wire slidably disposed in a containment tube, the first actuating member has first and second portions that are moveable relative to one another in the longitudinal directions, and the step of moving the capture tool from the retracted position to the extended position further includes moving the second portion relative to the first portion to slide a distal portion of the grasping wire out from the containment tube so that the distal portion of the grasping wire changes from a linear shape to a hook shape.

* * * * *